United States Patent
Fine et al.

(10) Patent No.: US 12,098,207 B2
(45) Date of Patent: Sep. 24, 2024

(54) ANTI-IL-36R ANTIBODIES FOR THE TREATMENT OF PYODERMA GANGRENOSUM

(71) Applicant: Boehringer Ingelheim International GmbH, Ingelheim am Rhein (DE)

(72) Inventors: Jay Fine, Mount Kisco, NY (US); Janine Lamar, Ingelheim am Rhein (DE); Steven John Padula, Wiesbaden (DE); Meera Ramanujam, Danbury, CT (US); Sudha Visvanathan, Hartsdale, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 287 days.

(21) Appl. No.: 17/376,233

(22) Filed: Jul. 15, 2021

(65) Prior Publication Data

US 2022/0073628 A1 Mar. 10, 2022

Related U.S. Application Data

(60) Provisional application No. 63/053,129, filed on Jul. 17, 2020.

(51) Int. Cl.
| | |
|---|---|
| *C07K 16/28* | (2006.01) |
| *A61K 39/395* | (2006.01) |
| *A61P 17/00* | (2006.01) |
| *A61K 39/00* | (2006.01) |

(52) U.S. Cl.
CPC ...... *C07K 16/2866* (2013.01); *A61K 39/3955* (2013.01); *A61P 17/00* (2018.01); *A61K 2039/505* (2013.01); *C07K 2317/24* (2013.01); *C07K 2317/565* (2013.01); *C07K 2317/76* (2013.01)

(58) Field of Classification Search
CPC ............ C07K 16/2866; C07K 2317/76; C07K 2317/565; C07K 2317/56; C07K 14/705; C07K 14/7155; A61K 39/395; A61K 2039/505; A61K 39/3955
See application file for complete search history.

(56) References Cited

U.S. PATENT DOCUMENTS

| | | | |
|---|---|---|---|
| 5,595,756 A | 1/1997 | Bally et al. | |
| 6,416,973 B1 | 7/2002 | Bakker et al. | |
| 6,953,843 B2 | 10/2005 | Bakker et al. | |
| 7,332,574 B2 | 2/2008 | Bakker et al. | |
| 8,034,771 B2 | 10/2011 | Sims et al. | |
| 8,481,021 B2 | 7/2013 | Sims et al. | |
| 9,023,995 B2 | 5/2015 | Brown et al. | |
| 9,334,320 B2 | 5/2016 | Okun et al. | |
| 10,526,410 B2 * | 1/2020 | Bowers | C07K 16/2866 |
| 11,730,812 B2 * | 8/2023 | Denkinger | C07K 16/2866 424/133.1 |
| 2004/0110930 A1 | 6/2004 | Reinl et al. | |
| 2004/0132085 A1 | 7/2004 | Bakker et al. | |
| 2004/0177391 A1 | 9/2004 | Bakker et al. | |
| 2005/0084900 A1 | 4/2005 | Bakker et al. | |
| 2007/0041905 A1 | 2/2007 | Hoffman et al. | |
| 2007/0071675 A1 | 3/2007 | Wu et al. | |
| 2008/0171035 A1 | 7/2008 | Bakker et al. | |
| 2008/0292623 A1 | 11/2008 | Bakker et al. | |
| 2009/0263403 A1 | 10/2009 | Bakker et al. | |
| 2010/0129374 A1 | 5/2010 | Bakker et al. | |
| 2010/0150945 A1 | 6/2010 | Bigler et al. | |
| 2010/0221252 A1 | 9/2010 | Bigler et al. | |
| 2011/0110852 A1 | 5/2011 | Miller et al. | |
| 2011/0159011 A1 | 6/2011 | Carrier et al. | |
| 2012/0121580 A1 | 5/2012 | Bhambhani et al. | |
| 2012/0177647 A1 | 7/2012 | Bigler et al. | |
| 2012/0244158 A1 | 9/2012 | Brige et al. | |
| 2013/0186797 A1 | 7/2013 | Walsh et al. | |
| 2013/0236471 A1 | 9/2013 | Brown et al. | |
| 2017/0355756 A1 | 12/2017 | Julien et al. | |
| 2018/0094065 A1 * | 4/2018 | Bowers | A61P 37/06 |
| 2018/0273627 A1 | 9/2018 | Boecher et al. | |
| 2019/0028285 A1 | 1/2019 | Cheng | |
| 2019/0284273 A1 | 9/2019 | Boecher et al. | |
| 2019/0284285 A1 | 9/2019 | Thoma et al. | |
| 2020/0015462 A1 * | 1/2020 | Murphy | C07K 14/7155 |
| 2020/0017592 A1 | 1/2020 | Fairhurst et al. | |
| 2020/0207862 A1 | 7/2020 | Baum et al. | |
| 2022/0356258 A1 * | 11/2022 | Wucherpfennig | C07K 16/2866 |

(Continued)

FOREIGN PATENT DOCUMENTS

| | | |
|---|---|---|
| EP | 1003861 A2 | 5/2000 |
| EP | 1627927 A2 | 2/2006 |
| EP | 2152750 A1 | 2/2010 |

(Continued)

OTHER PUBLICATIONS

Alavi et al. Spesolimab for hidradenitis suppurative: a proof-of-concept study. J Am Acad Dermatol 89(3): AB89, Sep. 2023.*

Belato et al. Response to: "Interleukin-36 in hidradenitis suppurativa: evidence for a distinctive proinflammatory role and a key factor in the development of an inflammatory loop". Brit J Dermatol 178: 807, 2018.*

Gouin et al. Transgenic Kallikrein 14 Mice Display Major Hair Shaft Defects Associated with Desmoglein 3 and 4 Degradation, Abnormal Epidermal Differentiation, and IL-36 Signature. J Invest Dermatol 140: 1184-1194, Jun. 2020.*

"Spesolimab" entry in IUPHAR/BPS Guide to Pharmacology. www.guidetopharmacology.org/GRAC/LigandDisplayForward?tab=clinical&ligandId=12169; accessed Jan. 26, 2024.*

(Continued)

*Primary Examiner* — Bridget E Bunner
(74) *Attorney, Agent, or Firm* — Wendy M. Gombert

(57) ABSTRACT

The present invention provides methods for treating, preventing or ameliorating a neutrophilic dermatosis. The methods of the present invention include administering to a patient suffering from a neutrophilic dermatosis a pharmaceutical composition including an anti-interleukin-36 receptor (anti-IL-36R) antibody.

8 Claims, 2 Drawing Sheets

Specification includes a Sequence Listing.

(56) References Cited

U.S. PATENT DOCUMENTS

2022/0402998 A1    12/2022    Liu et al.

FOREIGN PATENT DOCUMENTS

| | | |
|---|---|---|
| EP | 2176294 A1 | 4/2010 |
| EP | 2337799 A2 | 6/2011 |
| JP | 2009521933 A | 6/2009 |
| JP | 2016531123 A | 10/2016 |
| JP | 2017114829 A | 6/2017 |
| WO | 9856418 A1 | 12/1998 |
| WO | 9906557 A2 | 2/1999 |
| WO | 2004091658 A1 | 10/2004 |
| WO | 2008033333 A2 | 3/2008 |
| WO | 2008133857 A1 | 11/2008 |
| WO | 2009006112 A1 | 1/2009 |
| WO | 2010025369 A2 | 3/2010 |
| WO | 2013074569 A1 | 5/2013 |
| WO | 2016168542 A1 | 10/2016 |
| WO | 2019177883 A2 | 9/2019 |
| WO | 2019177888 A1 | 9/2019 |
| WO | 2020136101 A1 | 7/2020 |
| WO | 2020185479 A1 | 9/2020 |

OTHER PUBLICATIONS

Hessam et al. Interleukin-36 in hidradenitis suppurativa: evidence for a distinctive proinflammatory role and a key factor in the development of an inflammatory loop. Brit J Dermatol 178: 591-592, 2018.*

Malik et al. Ichthyosis molecular fingerprinting shows profound TH17 skewing and a unique barrier genomic signature. J Allergy Clin Immunol 143: 604-618, 2019.*

Navarini et al. Neutrophilic dermatoses and autoinflammatory diseases with skin involvement—innate immune disorders. Semin Immunopathol 38: 45-56, 2016.*

Polesie et al. Secukinumab in the Treatment of Generalized Pustular Psoriasis: A Case Report. Acta Derm Venereol 97: 124-125, 2017.*

Ma et al. Rapid response to spesolimab in a patient with severe refractory pyoderma gangrenosum. Clin Exp Dermatol 49(1): 82-84, 2024 (published Sep. 14, 2023).*

Clinical Trials, Interleukin-1 receptor-like 2 isoform a precursor, downloaded from https://ncbi.nlm.nlh.gov/protein/NP_003845.2?report+girevhist on Sep. 21, 2022 2022.

Elias, IL-36 in chronic inflammation and fibrosis, JCI, vol. 131, 2021, 14 pages.

Melton, Interleukin-36 Cytokine/Receptor Signaling, Int. J. of Molecular Sci., vol. 21, 2020, 22 pages.

Neufert, Rationale for IL-36 receptor antibodies in ulcertaive colitis, Expert opinion on Biological Therapy, vol. 20, 2020, 5 pages, https://doi.org/10.1080.14712598.2020.1695775.

Scheibe, Inhibiting Interleukin 36 receptor signaling reduces fibrosis in mice with chronic intestinal inflammation, Gastroenterology, vol. 156, 2019, 27 pages.

International Search Report and Written Opinion for PCT.US2022/074888 mailed Nov. 29, 2022.

International Search Report and Written Opinion for PCT/US2022/019743 mailed Oct. 21, 2022.

Baliwag, Cytokines in psoriasis, Cytokine, vol. 73, 2015, 9 pages.

Baum, Generalized Pustular psoriasis and palmoplantar pustulosis both slow upregulation of the IL-36, neutrophil chemokine, and innate pathways that are modulated by spesolimab, and anti-IL-36 receptor antibody treatment, Journal of Investigative Dermatology, Adaptive and Auto-Immunity, www.jidonline.org., vol. 140, 2020, p. S5.

Baum, Treatment with spesolimab, an anti-interleukin-36 receptor antibody, in patients with generalized pustular psoriasis, ESDR 2019 Annual Meeting, Retrieved from Internet: URL:https://www.sciencedirect.com/science/article/pii/S0022202X19322444/pdfft?md5=main.pdf on Jun. 23, 2022, 1 page.

Baum, Pustular psoriasis: molecular pathways and effects of spesolimab in generalized pustular psoriasis, Journal of Allergy and clinical immunology, vol. 149. 2021, p. 1402-1412.

Brenner, Gernalized pustular psoriasis induced by systemic glucocorticosteroids, Bristish Journal of Dermatology, vol. 161, 2009, p. 964-963.

Yuan, Biology of IL-36 Signaling and its role in systemic Inflammatory Diseases, Frontiers in Immunology, vol. 10, 2019, p. 2532.

Zeng, Integrated analysis of gene expression profiles identifies transciption factors potentially involved in psoriasis pathogenesis, J. of Cellular Biochem., vol. 120, 2019, p. 12582-12594.

Tortola, Psoriasiform dermatitis is driven by IL-36-mediated DC-keratinocyte crosstalk, The J. of Clinical Investigation, vol. 122, 2012, p. 3965-3976.

Foster, IL-36 promotes myeloid cell infiltration activation and inflammatory activity in skin, The j. of immunolgy, vol. 192, 2014, p. 6053-6061.

Swindell, 7th International Congress of psoriais: from gene to clinic: The Queen Elizabeth II Conference Centre, London, UK, Dec. 11-13, 2014, British Journal of Dermatology, vol. 171, 2014, 20 pages.

Kang, Rapid Formulation Development for Monoclonal Antibodies, BioProcess Chem., vol. 14, 2016, 4 pages.

Li, Spinal II-36/II-36R participates in the maintenance of chronic inflammatory pain through adtroglial JNK pathway, GLIA, vol. 67, 2019, Retrieved from the internet: URL: https://api.wiley.com/onlinelibrary.tdm/v1articles/10/1002Fglia.23552.

Alvarez, Imiquimod Treatment causes systemic disease in mice resembling generalized pustular psoriasis in an IL-1 and IL-36 Dependent Manner, GLIA, vol. 1, 2016, Retrieved from the Internet, URL:http://downloads.hindawi.com/journals/mi2016/6756138/xml.

Ratnarajah, Spesolimab, a novel treatment for pustular psoriasis, Journal od cutaneous med and surgery, vol. 24, 2020, Retrieved from the internet, URL:http://jouranls.sagepub.com/doi/full-xml/10.1177/1203475419888862.

Ly, Diagnosis and screening of patients with generalized pustular psoriasis, Psoriasis, Targets and Therapy, vol. 9, 2019, p. 37-42.

Vajdos, Comprehensive Functional Maps of the Antigen binding site of an Anti-ErbB2 Antibody obtained with shotgun Scanning Mutagenesis, J. Mol. Biol., vol. 320, 2002, p. 415-428.

Brown, Tolerance to single, but not multiple, amino acid replacements in antibody Vh CDR2, J. Immunol., vol. 320, 1996, p. 3285-3291.

Waiker, Imperfect Gold Standards for Kidney Injury Biomarker Evaluation, J. Am. Soc. Nephrol. vol. 23, 2012, p. 13-21.

Ganesan, Generation and functional characterization of anti-human and anti-mouse IL-36R antagonist monoclonal antibodies, MABS, vol. 9, 2017, p. 143-154.

Kazumitsu, The majority of generalized pustular psoriasis without psoriasis vulgaris is caused by deficiency of interleukin-36 receptor antagonist, vol. 133, 2013, p. 514-521.

A study to test how effective and safe different doses of BI 655130 are in patients with a moderate to severe form of the skin disease palmoplantar pustulosis. ClinicalTrials.gov identifier:NCT4015518. Jul. 9, 2019. Accessed May 19, 2023. https://clinicaltrials.gov/ct2/history/NCT04015518?V_5=V(Year2019).

Freitas, Screening and Treatment of Patients with palmoplantar Pustolosis (PPP): A review of current practices and recommendations. Clinical Cosmet. Invest. Dermatol., vol. 13, 2020, p. 561-578.

Walpole, The weight of nations, BMC Public Health, vol. 12, 2012, 6 pages.

Edwards, The remarkable flexibility of the human antibody repertoire, J, Mole. Biol., vol. 1, 2003, p. 103-118.

Almagro, Humanization of antibodies, Front Biosci., vol. 13, 2008, p. 1619-33.

Kussie, A single engineered amino acid substitution changes antibody fine specificity, J. Immunol., vol. 1, 1994, p. 146-52.

Anonymous, A study in patients with atopic eczema to test how effective BI655130 is and how well it is tolerated, Retrieved from the internet, http:/clinicaltrials.gov.ct2/show/record/NCT3822832/ retrieved Aug. 16, 2021.

(56) References Cited

OTHER PUBLICATIONS

Clinical Trials, A study in patients with Mild or moderate Ulcerative colitis who take a TNF inhibitor, History of changes for study, NCT103123120, Oct. 15, 2021.

International Report on Patentability for PCT/US2022/019742.

Nolan, S. et al. "505 Therapeutic activity of an anti-IL36R blocking antibody in inhibiting atopic dermatitis-like skin inflammation in mice" (2019) Journal of Investigative Dermatology, Society for Investigative Dermatology (SID) 2019, Meeting Abstract Supplement, 2 pgs.

Patrick, Garrett et al. "Epicutaneous *Staphylococcus aureaus* induces IL-36 to enhance IgE production and ensuing allergic disease" (2021) The Journal of Clinical Investigation, 1-15.

Puar, Neha et al. "New treatments in atopic dermatitis" (2020) Annals Allergy Asthma Immunology, 126, 21-21.

Qin, Jian-Zhong et al. "Role of NF-κB in the Apoptotic-resistant Phenotype of Keratinocytes" (1999) vol. 274, No. 53, 37957-37964.

Ramadas, Ravisankar A. et al. "IL-36a Exerts Pro-Inflammatory Effects in the Lungs of Mice" PLOS one (2012) vol. 7, Issue 9, e45784, 17 pgs.

Ramadas, Ravisankar A. et al. "Interleukin-1 Family Member 9 Stimulates Chemokine Production and Neutrophil Influx in Mouse Lungs" Am J Respir Cell Mol Biol (2011) vol. 44, pp. 134-145.

Russell, SE et al. "IL-36a expression is elevated in ulcerative colitis and promotes colonic inflammation" (2016) Mucosal Immunology, vol. 9, No. 5, 1193-1204.

Satoh T K et al "Are neutrophilic dermatoses autoinflammatory disorders?" (2018) The British Journal of Dermatology, vol. 178, No. 3, pp. 603-613.

Scheibe, Kristina et al. "Inhibiting Interleukin 36 Receptor Signaling Reduces Fibrosis in Mice with Chronic Intestinal Inflammation" (2019) Gastroenterology, vol. 156, No. 4, 1082-1097.

Steidl et al., "In vitro affinity maturation of human GM-CSF antibodies by targeted CDR-diversification", Mol. Immunol, 2008, vol. 46, pp. 135-144.

Su, Zhi et al. "IL-36 receptor antagonistic antibodies inhibit inflammatory responses in preclinical models of psoriasiform dermatitis" (2019) Experimental Dermatology, 28, 113-120.

Tortola, Luigi et al. "Psoriasiform dermatitis is driven by IL-36-mediated DC-keratinocyte crosstalk" The Journal of Clinical Investigation (2012) vol. 122, No. 11, pp. 3965-3976.

Towne, Jennifer E. et al. "Interleukin (IL)-1F6, IL-1F8, and IL-1F9 Signal through IL-1Rrp2 and IL-1RAcP to Activate the Pathway Leading to NF-kB and MAPKs" The Journal of Biological Chemistry (2004) vol. 279, No. 14, pp. 13677-13688.

Towne, Jennifer E. et al. "Interleukin-36 (IL-36) Ligands Require Processing for Full Agonist (IL-36a, IL-36b, and IL-36g) or Antagonist (IL-36Ra) Activity" The Journal of Biological Chemistry (2011) vol. 286, No. 49, pp. 42594-42602.

Tsai, Ya-Chu et al. "Anti-interleukin and interleukin therapies for psoriasis: current evidence and clinical usefulness" (2017) Therapeutic Advances in Musculoskeletal Disease, vol. 9 (11), 277-294.

Vajdos et al., "Comprehensive Functional Maps of the Antigenbinding Site of an Anti-Erb82 Antibody Obtained with Shotgun Scanning Mutagenesis", J. Mol. Biol., 2002, 320, pp. 415-428.

Wang, Wei et al. "Antibody Structure, Instability and Formulation" (2007) Journal of Pharmaceutical Sciences, vol. 96, No. 1, 1-26.

Warzocha, Krzysztof et al. "Antisense Strategy: Biological Utility and Prospects in the Treatment of Hematological Malignancies" (1997) Leukemia and Lymphoma, vol. 24, 267-281.

Wong, Chi Heem et al. "Estimation of clinical trial success rates and related parameters" (2019) Biostatistics, 20, 2, 273-286.

Aagaard, Lars et al. "RNAi therapeutics: Principles, prospects and challenges" (2007) Advanced Drug Delivery Reviews, vol. 59, 75-86.

Andoh, Akira et al. "Increased Expression of Interleukin-36 in the Inflamed Mucosa of Inflammatory Bowel Disease" Abstract 1812, (2015) The American Journal of Gastroenterology, vol. 110, Supplement 1, S770.

Anonymous Anti-IL36 gamma/IL-1 F9 antibody (OT12F4) (ab156783), Jan. 1, 2019, XP055650144, 6 pgs.

Arend, William P. et al. "IL-1, IL-18, and IL-33 families of cytokines" Immunological Reviews (2008) vol. 223, pp. 20-22.

Bachelez, Herve et al. "Inhibition of the Interleukin-36 Pathway for the Treatment of Generalized Pustular Psoriasis" (2019) The New England Journal of Medicine, 380: 10, 981-983.

Blumberg, Hal et al. "IL-1RL2 and Its Ligands Contribute to the Cytokine Network in Psoriasis" The Journal of Immunology (2010) vol. 185, pp. 4354-4362.

Blumberg, Hal et al. "Opposing activities of two novel members of the IL-1 ligand family regulate skin inflammation" The Journal of Experimental Medicine (2007) vol. 204, No. 11, pp. 2603-2614.

Body Mass Index Table from www.nhlbi.nih.gov/health/educational/lose_wt/BMI/bmi_tbl.pdf <http://www.nhlbi.nih.gov/health/educational/lose_wt/BMI/bmi_tbl.pdf>, viewed Sep. 16, 2021.

Boehringer Ingelheim "Boehringer Ingelheim R&D pushes to Transcend Disease Boundaries" (2018) Business Wire, 4 pgs.

Born, Teresa et al. "Identification and characterization of two members of a novel class of the interleukin-1 receptor (IL-1R) family. Delineation of a new class of IL-1R-related proteins based on signaling" The Journal of Biological Chemistry (2000), vol. 275, pp. 29946-29954.

Bowie, James U. et al. "Deciphering the Message in Protein Sequences: Tolerance to Amino Acid Substitutions" Science (1990) vol. 247, pp. 1306-1310.

Brown et al, "Tolerance to Single, but Not Multiple, Amino Acid Replacements in Antibody VH CDR2", J. Immunol., 1996, 156, pp. 3285-3291.

Burgess, Wilson H. et al. "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue" Journal of Cell Biology, (1990) vol. 111, pp. 2129-2138.

Chang, Byeong S. et al. "Practical Approaches to Protein Formulation Development" (2022) Kluwer Academic/ Plemum publishers, 1-25.

Chustz, Regina T. et al. "Regulation and Function of the IL-1 Family Cytokine IL-1F9 in Human Bronchial Epithelial Cells" Am J Respir Cell Mol Biol (2011) vol. 45, pp. 145-153.

Clark, James D. et al. "Discovery and Development of Janus Kinase (JAK) Inhibitors for Inflammatory Diseases" (2014) American Chemical Society, 5023-5038.

Clinical Trials "A Study in Patients with Atopic Eczema to Test How Effective BI 655130 Is and How Well It Is Tolerated" (2021) Last Update Posted, NCT03822832, 11 pgs.

Clinical Trials "A Study to Evaluate the Efficacy and Safety of ANB019 in Subjects With Palmoplantar Pustulosis (PPP)" NCT03633396, (2019) clinicaltrails.gov, 8 pgs.

Clinical Trials "BI655130 Single Dose in Generalized Pustular Psoriasis" (2018) Identifier: NCT02978690, 6 pgs.

Clinical Trials "History of Changes for Study: NCT03135548, Initial Dosing of BI 655130 in Palmoplantar Pustulosis Patients" (2020) clinicaltrials.gov, 5 pgs.

Clinical Trials "History of Changes for Study: NCT03782792, A Study to Test BI 655130 in Patients iwth Flare-up of a Skin Disease called Generalized Pustular Psoriasis" (2018) clinicaltrials.gov, 6 pgs.

Clinical Trials "This Study Tests How BI 655130 Works in Patients with Active Ulcerative Colitis. The Study also Tests how well BI 655130 is Tolerated and Whether it Helps the Patients" (2020) NCT03100864, 28 pgs.

Creative Diagnostics "Mouse anti-IL1RL2 Monoclonal Antibody" Product Information. Gene ID 8808. mRNA Ref Seq NM_003854. (2004).

Debets, Reno et al. "Two Novel IL-1 Family Members, IL-1d and IL-1e Function as an Antagonist and Agonist of NF-kB Activation Through the Orphan IL-1 Receptor-Related Protein 21" The Journal of Immunology (2001) vol. 167, pp. 1440-1446.

Dinarello, Charles A. "Immunological and Inflammatory Functions of the Interleukin-1 Family" The Annual Review of Immunology (2009) vol. 27, pp. 519-550.

(56) References Cited

OTHER PUBLICATIONS

Dinarello, Charles et al. "IL-1 family nomenclature" Nature Immunology (2010) vol. 11, pp. 973-974.

Ding, Liping et al. "IL-36 cytokines in autoimmunity and inflammatory disease" (2018) Oncotarget, vol. 9, No. 2, 2895-2901.

Guido, Rafael V.C. et al. "Virtual Screening and Its Integration with Modern Drug Design Technologies" (2008) Current Medicinal Chemistry, vol. 15, 37-46.

International Search Report for PCT/US2012/064933 filed Nov. 14, 2012, mailed Feb. 7, 2013.

International Search Report for PCT/US2019/021296 mailed Feb. 27, 2020.

International Search Report PCT/EP2019/086521 mailed Apr. 6, 2020.

International Search Report PCT/US2018/024296 mailed Jun. 22, 2018.

International Search Report PCT/US2020/021059 mailed on Jun. 23, 2020.

International Search Report PCT/US2021/032713 mailed Aug. 30, 2021, 12 pgs.

International Search Report PCT/US2021/041734 mailed Nov. 11, 2021, 4 pgs.

Johnston, Andrew et al. "IL-1 and IL-36 are dominant cytokines in generalized pustular psoriasis" (2017) J Allergy Clin Immunol, 109-120.

Johnston, Andrew et al. "IL-1F5,—F6,—F8, and—F9: A Novel IL-1 Family Signaling System that is Active in Psoriasis and Promotes Keratinocyte Antimicrobial Peptide Expression" The Journal of Immunology (2011) vol. 186, pp. 2613-2622.

Lacy, et al. "Correlation between Antibody Affinity and Activity: Understanding the Molecular Basis for a Picomolar to Femtomolar Increase in Affinity" (2009) Abstract, 1621—Pos, Board B465, vol. 96, Issue 3, S1, 317a-318a.

Lazar, Eliane et al. "Transforming Growth Factor a: Mutation of Aspartic Acid 47 and Leucine 48 Results in Different Biological Activities" Molecular and Cellular Biology (1988) vol. 8, No. 3, pp. 1247-1252.

Lingel, Andreas et al. "Structure of IL-33 and its Interaction with the ST2 and IL-1RAcP Receptors—Insight into Heterotrimeric IL-1 Signaling Complexes" Structure (2009) vol. 17, pp. 1398-1410.

Lovenberg, Timothy W. et al. "Cloning of a cDNA encoding a novel interleukin-1 receptor related protein (IL 1R-rp2)" Journal of Neuroimmunology, (1996) vol. 70, pp. 113-122.

Magne, David et al. "The new IL-1 Family Member IL-1F8 stimulates production of inflammatory mediators by synovial fibroblasts and articular chondrocytes" Arthritis Research & Therapy (2006) vol. 8:R80, 11 pgs.

Marrakchi, Slaheddine et al. "Interleukin-36-Receptor Antagonist Deficiency and Generalized Pustular Psoriasis" New England Journal of Medicine (2011) vol. 365 pp. 620-628.

Marzano Angelo V. et al: "Mechanisms of Inflammation in Neutrophil-Mediated Skin Diseases", (2019) Frontiers in Immunology, vol. 18, 2019, p. 1859.

Matsuba et al., "Preparation of Super-High Affinity Rabbit Monoclonal Antibodies Against Estradiol.: Application to Highly Sensitive Estradiol Measurement", TOSOH Research & Technol. Review. 2008, vol. 52, pp. 3-9.

Mckeaugue, Maureen et al. "Challenges and Opportunities for Small Molecule Aptamer Development" (2012) Journal of Nucleic Acids, Article ID: 748913, 20 pgs.

Mcmahan, Catherine J. et al. "A Novel IL-1 receptor, cloned from B cells by mammalian expression, is expressed in many cell types" EMBO Journal (1991) vol. 10, No. 10, pp. 2821-2832.

Mrowietz Ulrich et al: "Spesolimab, an Anti-Interleukin-36 Receptor Antibody, in Patients with Palmoplantar Pustulosis: Results of a Phase IIa, Multicenter, Double-Blind, Randomized, Placebo-Controlled Pilot Study", (2021) Dermatology and Therapy, vol. 11, No. 2, 571-585.

NCBI GENE databases (IL1RL2 interleukin 1 receptor-like 2 [Homo sapiens (human)]; http:www.ncbi.nlm.nib.gov/gene/8808; downloaded May 18, 2014, 8 pgs.

Nishida, Atsushi et al. "Increased Expression of Interleukin-36, a Member of the Interleukin-1 Cytokine Family, in Inflammatory Bowel Disease" (2016) Inflamm Bowel Dis, vol. 22, No. 2, 303-314.

Clinical Trials, A study in patients with atopic eczema to test how effective BI 655130 is and how well it is tolerated, 2019; NCT03822832, p. 1470-1492.

Berke, Atopic Dermatitis, American Family Physician, vol. 86, 2012, p. 35-42.

Costanzo, Pustular psoriasis with a focus on generalized pustualr psoriasis, Italian J. of Dermatology and Venereology, vol. 157, 2022, p. 489-96.

Tsai, Anti-interleukin and interleukin therapies for psoriasis, Ther. Adv. Muscoloskel. Dis. vol. 9, 2017, p. 277-294.

Kimball, Adalimumab for the treatment of moderate to severe hidradentitis Suppurativa, Annals of internal Medicine, vol. 157, 2012, p. 846-865.

Wark, The microbiome in Hidradentitis Suppurativa, A review, Dermatol., Thera., vol. 11, 2021, p. 39-52.

Frew, The effect of subcutaneous brodalumab on clinical disease activity in hidraenitis suppurativa, J. Am. Acad Derma., vol. 5, 2020, p. 1341-1348.

Glatt, Efficacy and Safety of Bimekizumab in Moderate to severe Hidradenitis Suppurativa, vol. 157, 2021, p. 1279-1288.

Li, Construction strategies for developing expression vectors for recombinant monoclonal antibody production in CHO cells, Molecular Biology Reports, vol. 45, 2018, p. 2907-2912.

Byrd, Neutrophil extracellular traps, B cells, and type 1 interferons contribute to immune dysregulation in hidradenitis suppurativa, Science Translational Med., vol. 508, 2021, p. 1-12.

UCB announcement, UCB Announcement Positive Phase 3 studies for Bimekizumab in Hidradenitis Suppurativa, last updated Dec. 2022, 1 page.

Robins, Estimation of a common effect parameter from sparse follow-up data, Biometrics, vol. 51, 1985, p. 55-68.

Crommelin, Formulation of Biologics including Biopharmaceutical Considerations, Utrect Institute, vol. 10, 2019, p. 83-103.

Flood, Biologic Treatment for Hidradenitis Suppurativa, Am. J. of Clinical Derma., vol. 20, 2019, p. 625-638.

Phan, Global prevalence of hidradenitis suppurativa and geograhical variation, Biomedical Derma., vol. 10, 2020, p. 1-6.

Highet, Streptoccus milleri causing treatable infection in perineal hidradenitis suppurativa, British J. of Derma., vol. 103, 1980, p. 375-382.

Zouboulis, Development and validation of the International Hidradenitis Suppurativa severity score system, British J. of Derma., vol. 177, 2017, p. 1401-1409.

Revillet, The microbiological landscape of Anaerobic infections in Hidradenitis Suppurativa, Clinical Infectious Diseases, vol. 65, 2017, p. 282-291.

Yellen, Measuring fatigue and other anemia related symptoms with the functional assessment of cancer therapy, J. of Pain and Symptom management, vol. 13, 1997, p. 63-74.

Zouboulis, European S1 guideline for the treatment of hidradenitis suppurativa, JEADV, vol. 10, 2015, p. 619-644.

Kimball, HiSCR a novel clinical endpoint to evaluate therapeutic outcomes in patients with hidradenitis suppurativa, JEADV, vol. 10, 2016, p. 989-994.

Harusato, IL-36y signaling controls the induced regulatory T-cell Th9 cell balance via NFkB activation and STAT transcription factors, Mucosal Immunolgoy, vol. 10, 2017, p. 1455-1467.

Marrakechi, Interleukin-36-Receptor Antagonist Deficieny and Generalized Pustular Psoriasis, The N. E. Journal of Medicine, vol. 365, 2011, p. 10-18.

Marrakechi, Inhibition of the Interleukin-36 Pathway for the treatment of Generalized Pustular Psoriasis, The New England Journal of Medicine, vol. 380, 2019, p. 620-628.

Taylor, A transgenic mouse tat expresses a diversity of human sequence heavy and light chain immunoglobulins, Nucleic Acids Research, vol. 20, 1992, p. 6287-6295.

(56) References Cited

OTHER PUBLICATIONS

Rankin, Case report of hidradenitis suppurativa, SAGE Medical Case reports, vol. 9, 2021, p. 1-4.
Cella, Validation of the Functional assessment of chronic illness therapy fatigue scale relative to other instumentation in patients with rheumatoid arthritis, J. of Rheumatology, vol. 32, 2015, p. 811-819.
Woodworth, Standardizing assessment and reporting of adverse effects in rheumatology clinical trials II, J. of Rheumatology, vol. 34, 2007, p. 1401-1414.
Calabrese, Opportunistic infections and biologic therapies in immune-mediated inflammatory diseases, Research gate, Annals of Rheumatic Diseases, vol. 10, 2015, p. 1-10.
Moltrasio, Hidredenitis Suppurativa, A perspective on genetic factors involved in the disease, Biomedicines, vol. 10, 2022, p. 2039-2053.
Greenland, Estimation of a common effect parameter from a sparse foll up data, Biometrics, vol. 41, 1985, p. 55-68.
Anon, Research Letter, British J. of Derma., vol. 173, 2015, p. 1546-1549.
Krueger, Hidradenitis suppurativa, new insights into disease mechanisms, Br. J. Derma., vol. 190, 2023, p. 149-162.
Hessam, Interleukin-36 in hidradenitis suppurativa, evidence for a distinctive proinflammatory role and a key factor in the development of an inflammatory loop, B. Journal of Derma., vol. 178, 2018, p. 761-767.
Scala, Hidradenitis Suppurativa, Where we are and where we are going, Cells, vol. 10, 2021, p. 3390-3409.
Zouboulis, Hidradenitis Suppurativa Acne Inversa: criteria for diagnosis, Dermatology, vol. 231, 2015, p. 184-190.
Ring, The Follicular skin microbiome in patients with Hidradenitis Suppurativa and healthy controls, JAMA derma., vol. 153, 2017, p. 897-905.
Towne, Interleukin (IL)-1F6, IL-1F8, and IL-1F9 signal through IL-1Rrp2 and IL-1RacP to activate the pathway leading to NF-KB and MAPKs, The J. of Biological Chem, vol. 14, 2004, p. 42594-42602.
Sarkissian, Identification of Biomarkers and critical Eval. of Biomarker validation in Hidradentitis Suppurativa, JAMA Derma., vol. 158, 2022, p. 300-313.
Towne, Interleukin-36 (IL 36) ligands require processing for full agonist, J. of Biological Chemistry, vol. 286, 2011, p. 13677-13688.
Gao, Inversa acne a case report and ID of the locus at Chromosome 1p21.2-1q25.3, J. of investigative Derma., vol. 136, 2006, p. 1302-1306.
Suzuki, Phosphorylation in Epidermal Stem cells, vol. 132, 2012, p. 2459-2461.
Dinarello, A clinical Perspective of IL-1B as the gatekeeper of inflammation, Euro. J. of Immunology, vol. 41, 2011, p. 1203-1217.
Webster, The Functional Assessment of Chronic Illness Therapy Measurement system, Bio Med Central, vol. 79, 2003, p. 73-79.
Di Caprio Il-36 cytokines are increased in acne, Arch. Dermatol. Res., vol. 10, 2017, p. 673-678.
Van Straalen, Contribution of genetics to the susceptibility to hidradenitis suppurativa in a large, cross sectional dutch twin cohort, JAMA derma, vol. 156, 2020, p. 1359-1362.
Navrazhina, E pithelialized tunnels are a source of inflammation in hidradenitis suppurativa, J. Allergy Clin. Immunol., vol. 12, 2020, p. 2213-2224.
Thomi, Increased expression of the interleukin-36 cytokines in lesions of hidradenitis suppurativa, JEADV, vol. 31, 2017, p. 2091-2096.
Jorgensen, Clinical, microbiological, immunological and imaging characteristics of tunnels and fistulas in hidradenitis suppurativa, Experimental Dermatology, vol. 29, 2019, p. 118-123.
Revillet, Bacterial pathogens associated with Hidradenitis Suppurativa, France, Emerginv infectious diseases, vol. 20, 2014, p. 1990-1998.
Winthrop, Opportunistic infections and biologic therapies in immune mediated inflammatory diseases, vol. 1, 2015, p. 1-12.
Bonnekoh, Spectrum of genetic autoinflammatory diseases presenting with cutaneous symptoms, Acta Derm Venereol., vol. 100, 2020, p. 140-151.
Bai, Studies of mouse models of allergic disease, Chinese Journal of Comparative Medicine, vol. 2, 2020, p. 128-134, Abstract only.
Anon, Anaptybio Reports Harp Phase 2 top-line data of imsidolimab in moderate to severe hidradenitis suppurativa, Anaptysbio, 2016, p. 1-6.
Weiss, Neutrophilic Dermatoses, Current Dermatology Reports, vol. 11, 2022, p. 89-102.
Hunt, The current clinical trial landscape for hidradenitis suppurativa, vol. 13, 2023, p. 1391-1407.
Ferrante, Safety and tolerability of speso in patients with ulcertaive colitis, Exp. Opinion on drug safety, vol. 2, 2023, p. 141-152.
Bissonnette, Speso, an anti-interleukin-36 receptor antibody, in patients with moderate ro severe atopic dermatitis, JEADV, vol. 10, 2022, p. 649-652.
Guenin, Spesolimab use in treatment of pyoderma gangrenosum, JAAD, vol. 10, 2023, p. 18-23.
Alavi, Pyoderma Gangroenosum,Am. J. Clin. Dermatol, vol. 18, 2017, p. 355-372.
Mrowietz, Spesolimab, an anti-interleukin-36 receptor antibody, Dermatol. Ther., 2020, published online https://doi/org/10.1007/s13555-021-00504-0, p. 571-585.

* cited by examiner

SEQUENCE LISTING

```
<160> NUMBER OF SEQ ID NOS: 142

<210> SEQ ID NO 1
<211> LENGTH: 108
<212> TYPE: PRT
<213> ORGANISM: Mus sp.

<400> SEQUENCE: 1

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Ser
            20                  25                  30

Tyr Leu His Trp Tyr Gln Lys Lys Pro Gly Ser Ser Pro Lys Leu Trp
        35                  40                  45

Val Tyr Ser Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln His Arg Ser Pro
                85                  90                  95

Val Thr Phe Gly Ser Gly Thr Lys Leu Glu Met Lys
                100                 105

<210> SEQ ID NO 2
<211> LENGTH: 107
<212> TYPE: PRT
<213> ORGANISM: Mus sp.

<400> SEQUENCE: 2

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
            20                  25                  30

Leu Ala Trp Tyr Gln Gln Arg Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Gln Phe Ser Phe Asn Ile Arg Ser Leu Gln Ala
65                  70                  75                  80

Glu Asp Phe Ala Ser Tyr Tyr Cys Gln Gln Val Tyr Thr Thr Pro Leu
                85                  90                  95

Thr Phe Gly Gly Gly Thr Lys Leu Glu Ile Lys
                100                 105

<210> SEQ ID NO 3
<211> LENGTH: 107
<212> TYPE: PRT
<213> ORGANISM: Mus sp.

<400> SEQUENCE: 3

Asp Ile Gln Met Thr Gln Ser Pro Ala Ser Gln Ser Ala Ser Leu Gly
1               5                   10                  15
```

```
Glu Ser Val Thr Phe Thr Cys Leu Ala Ser Gln Thr Ile Gly Thr Trp
                20                  25                  30

Leu Gly Trp Tyr Gln Gln Lys Pro Gly Lys Ser Pro Gln Leu Leu Ile
            35                  40                  45

Tyr Arg Ser Thr Thr Leu Ala Asp Gly Val Pro Ser Arg Phe Ser Gly
 50                  55                  60

Ser Gly Ser Gly Thr Lys Phe Ser Phe Lys Ile Ser Ser Leu Gln Ala
 65                  70                  75                  80

Ala Asp Phe Ala Ser Tyr Tyr Cys Gln Gln Leu Tyr Ser Ala Pro Tyr
                85                  90                  95

Thr Phe Gly Gly Gly Thr Lys Leu Glu Ile Arg
                100                 105
```

<210> SEQ ID NO 4
<211> LENGTH: 112
<212> TYPE: PRT
<213> ORGANISM: Mus sp.

<400> SEQUENCE: 4

```
Asp Val Leu Leu Thr Gln Thr Pro Leu Ser Leu Pro Val Ser Leu Gly
 1               5                  10                  15

Asp Gln Ala Ser Ile Ser Cys Arg Ser Ser Gln Asn Ile Val His Ser
                20                  25                  30

Asn Gly Asn Thr Tyr Leu Gln Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ala Gly Thr Lys Leu Glu Leu Lys
                100                 105                 110
```

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Tyr Lys Tyr
                20                  25                  30

Leu Asn Trp Tyr Gln Gln Lys Pro Asp Gly Thr Leu Lys Leu Leu Ile
            35                  40                  45

Tyr Tyr Thr Ser Gly Leu His Ser Gly Val Pro Ser Arg Phe Ser Gly
 50                  55                  60

Ser Gly Ser Gly Thr Asp Phe Ser Leu Thr Ile Ser Asn Leu Glu Pro
 65                  70                  75                  80

Glu Asp Ile Ala Thr Tyr Phe Cys Gln Gln Asp Ser Lys Phe Pro Trp
                85                  90                  95

Thr Phe Gly Gly Asp Thr Lys Leu Glu Ile Lys
                100                 105
```

<210> SEQ ID NO 6
<211> LENGTH: 108
<212> TYPE: PRT
<213> ORGANISM: Mus sp.

<400> SEQUENCE: 6

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Phe His Trp Tyr Gln Gln Lys Pro Gly Ser Ser Pro Lys Leu Trp
        35                  40                  45

Ile Tyr Arg Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Phe His Arg Ser Pro
                85                  90                  95

Leu Thr Phe Gly Ala Gly Thr Lys Leu Glu Leu Lys
            100                 105

<210> SEQ ID NO 7
<211> LENGTH: 107
<212> TYPE: PRT
<213> ORGANISM: Mus sp.

<400> SEQUENCE: 7

Asp Ile Val Met Thr Gln Ser Gln Lys Phe Leu Ser Thr Ser Val Gly
1               5                   10                  15

Val Arg Val Ser Val Thr Cys Lys Ala Ser Gln Asp Val Gly Thr Asn
            20                  25                  30

Val Leu Trp Tyr Gln Gln Lys Ile Gly Gln Ser Pro Lys Pro Leu Ile
        35                  40                  45

Tyr Ser Ala Ser Tyr Arg His Ser Gly Val Pro Asp Arg Phe Thr Gly
    50                  55                  60

Ser Gly Ser Gly Thr Asp Phe Thr Leu Ile Ile Ser Asn Val Gln Ser
65                  70                  75                  80

Glu Asp Leu Ala Glu Tyr Phe Cys Gln Gln Tyr Ser Arg Tyr Pro Leu
                85                  90                  95

Thr Phe Gly Pro Gly Thr Lys Leu Glu Leu Lys
            100                 105

<210> SEQ ID NO 8
<211> LENGTH: 107
<212> TYPE: PRT
<213> ORGANISM: Mus sp.

<400> SEQUENCE: 8

Asp Ile Val Met Thr Gln Ser Gln Lys Phe Leu Ser Thr Ser Val Gly
1               5                   10                  15

Val Arg Val Ser Val Thr Cys Lys Ala Ser Gln Asp Val Gly Thr Asn
            20                  25                  30

Val Leu Trp Tyr Gln Gln Lys Ile Gly Gln Ser Pro Lys Ala Leu Ile
        35                  40                  45

Tyr Ser Ala Ser Tyr Arg His Ser Gly Val Pro Asp Arg Phe Thr Gly
    50                  55                  60

Ser Gly Ser Gly Thr Asp Phe Thr Leu Ile Ile Thr Asn Val Gln Ser

```
65                  70                  75                  80
Glu Asp Leu Ala Glu Tyr Phe Cys Gln Gln Tyr Ser Arg Tyr Pro Leu
                85                  90                  95

Thr Phe Gly Pro Gly Thr Lys Leu Glu Leu Lys
            100                 105

<210> SEQ ID NO 9
<211> LENGTH: 107
<212> TYPE: PRT
<213> ORGANISM: Mus sp.

<400> SEQUENCE: 9

Asp Ile Val Met Thr Gln Ser Gln Lys Phe Met Ser Ala Thr Val Gly
1               5                   10                  15

Gly Arg Val Asn Ile Thr Cys Lys Ala Ser Gln Asn Val Gly Arg Ala
            20                  25                  30

Val Ala Trp Tyr Gln Gln Lys Pro Gly Gln Ser Pro Lys Leu Leu Thr
        35                  40                  45

His Ser Ala Ser Asn Arg Tyr Thr Gly Val Pro Asp Arg Phe Thr Gly
    50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Asp Leu Lys
            100                 105

<210> SEQ ID NO 10
<211> LENGTH: 107
<212> TYPE: PRT
<213> ORGANISM: Mus sp.

<400> SEQUENCE: 10

Asp Ile Gln Met Thr Gln Ser Pro Ala Ser Gln Ser Ala Ser Leu Gly
1               5                   10                  15

Glu Ser Val Thr Phe Ser Cys Leu Ala Ser Gln Thr Ile Gly Thr Trp
            20                  25                  30

Leu Gly Trp Tyr Gln Gln Lys Pro Gly Lys Ser Pro Gln Leu Leu Ile
        35                  40                  45

Tyr Arg Ala Thr Ser Leu Ala Asp Gly Val Pro Ser Arg Phe Ser Gly
    50                  55                  60

Ser Gly Ser Gly Thr Asn Phe Ser Phe Lys Ile Ser Ser Leu Gln Ala
65                  70                  75                  80

Glu Asp Leu Ala Ser Tyr Tyr Cys Gln Gln Leu Tyr Ser Gly Pro Tyr
                85                  90                  95

Thr Phe Gly Gly Gly Thr Lys Leu Glu Ile Arg
            100                 105

<210> SEQ ID NO 11
<211> LENGTH: 119
<212> TYPE: PRT
<213> ORGANISM: Mus sp.

<400> SEQUENCE: 11

Gln Val Gln Leu Gln Gln Ser Gly Thr Glu Leu Leu Lys Pro Gly Ala
1               5                   10                  15

Ser Val Lys Leu Ser Cys Lys Ala Ser Gly Asn Thr Val Thr Ser Tyr
            20                  25                  30
```

```
Trp Met His Trp Val Lys Gln Arg Pro Gly Gln Gly Leu Glu Trp Ile
        35                  40                  45

Gly Glu Ile Leu Pro Ser Thr Gly Arg Thr Asn Tyr Asn Glu Asn Phe
 50                  55                  60

Lys Gly Lys Ala Met Leu Thr Val Asp Lys Ser Ser Thr Ala Tyr
65                   70                  75                  80

Met Gln Leu Ser Ser Leu Ala Ser Glu Asp Ser Ala Val Tyr Tyr Cys
                85                  90                  95

Thr Ile Val Tyr Phe Gly Asn Pro Trp Phe Ala Tyr Trp Gly Gln Gly
                100                 105                 110

Thr Leu Val Thr Val Ser Ala
            115

<210> SEQ ID NO 12
<211> LENGTH: 125
<212> TYPE: PRT
<213> ORGANISM: Mus sp.

<400> SEQUENCE: 12

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Asp Asn
            20                  25                  30

Tyr Met Asn Trp Val Arg Gln Ser His Gly Lys Ser Leu Glu Trp Ile
        35                  40                  45

Gly Arg Val Asn Pro Ser Asn Gly Asp Thr Lys Tyr Asn Gln Asn Phe
 50                  55                  60

Lys Gly Lys Ala Thr Leu Thr Val Asp Lys Ser Leu Ser Thr Ala Tyr
65                   70                  75                  80

Met Gln Leu Asn Gly Leu Thr Ser Glu Asp Ser Ala Val Tyr Tyr Cys
                85                  90                  95

Gly Arg Thr Lys Asn Phe Tyr Ser Ser Tyr Ser Tyr Asp Ala Met
                100                 105                 110

Asp Tyr Trp Gly Gln Gly Thr Ser Val Thr Val Ser Ser
            115                 120                 125

<210> SEQ ID NO 13
<211> LENGTH: 124
<212> TYPE: PRT
<213> ORGANISM: Mus sp.

<400> SEQUENCE: 13

Glu Val Gln Leu Gln Gln Ser Gly Ala Glu Phe Val Arg Pro Gly Ala
1               5                   10                  15

Ser Val Lys Phe Ser Cys Thr Ala Ser Gly Phe Asn Ile Lys Asp Asp
            20                  25                  30

Tyr Ile His Trp Val Arg Gln Arg Pro Glu Gln Gly Leu Glu Trp Val
        35                  40                  45

Gly Arg Ile Asp Pro Ala Asn Gly Asn Thr Lys Tyr Ala Pro Lys Phe
 50                  55                  60

Gln Asp Lys Ala Thr Ile Thr Ala Asp Thr Ser Ser Asn Thr Ala Tyr
65                   70                  75                  80

Leu Gln Leu Ser Ser Leu Thr Ser Glu Asp Thr Ala Val Tyr Tyr Cys
                85                  90                  95

Ala Lys Ser Phe Pro Asn Asn Tyr Tyr Ser Tyr Asp Asp Ala Phe Ala
                100                 105                 110
```

Tyr Trp Gly Gln Gly Thr Leu Val Thr Val Ser Ala
            115                 120

<210> SEQ ID NO 14
<211> LENGTH: 118
<212> TYPE: PRT
<213> ORGANISM: Mus sp.

<400> SEQUENCE: 14

Gln Val Gln Leu Lys Glu Ser Gly Pro Val Leu Val Ala Pro Ser Gln
1               5                   10                  15

Ser Leu Ser Ile Thr Cys Thr Val Ser Gly Phe Ser Leu Thr Lys Phe
            20                  25                  30

Gly Val His Trp Ile Arg Gln Thr Pro Gly Lys Gly Leu Glu Trp Leu
        35                  40                  45

Gly Val Ile Trp Ala Gly Gly Pro Thr Asn Tyr Asn Ser Ala Leu Met
    50                  55                  60

Ser Arg Leu Thr Ile Ser Lys Asp Ile Ser Gln Ser Gln Val Phe Leu
65                  70                  75                  80

Arg Ile Asp Ser Leu Gln Thr Asp Asp Thr Ala Met Tyr Tyr Cys Ala
                85                  90                  95

Lys Gln Ile Tyr Tyr Ser Thr Leu Val Asp Tyr Trp Gly Gln Gly Thr
            100                 105                 110

Ser Val Thr Val Ser Ser
        115

<210> SEQ ID NO 15
<211> LENGTH: 120
<212> TYPE: PRT
<213> ORGANISM: Mus sp.

<400> SEQUENCE: 15

Gln Val Gln Leu Lys Glu Ser Gly Pro Gly Leu Val Ala Pro Ser Gln
1               5                   10                  15

Ser Leu Phe Ile Thr Cys Thr Val Ser Gly Phe Ser Leu Ser Ser Tyr
            20                  25                  30

Glu Ile Asn Trp Val Arg Gln Val Pro Gly Lys Gly Leu Glu Trp Leu
        35                  40                  45

Gly Val Ile Trp Thr Gly Ile Thr Thr Asn Tyr Asn Ser Ala Leu Ile
    50                  55                  60

Ser Arg Leu Ser Ile Ser Lys Asp Asn Ser Lys Ser Leu Val Phe Leu
65                  70                  75                  80

Lys Met Asn Ser Leu Gln Thr Asp Asp Thr Ala Ile Tyr Tyr Cys Ala
                85                  90                  95

Arg Gly Thr Gly Thr Gly Phe Tyr Tyr Ala Met Asp Tyr Trp Gly Gln
            100                 105                 110

Gly Thr Ser Val Thr Val Ser Ser
        115                 120

<210> SEQ ID NO 16
<211> LENGTH: 119
<212> TYPE: PRT
<213> ORGANISM: Mus sp.

<400> SEQUENCE: 16

Gln Val Gln Leu Gln Gln Pro Gly Ala Asp Phe Val Arg Pro Gly Ala
1               5                   10                  15

```
Ser Met Arg Leu Ser Cys Lys Ala Ser Gly Tyr Ser Phe Thr Ser Ser
            20                  25                  30

Trp Ile His Trp Val Lys Gln Arg Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Lys Ala Thr Leu Thr Val Asp Lys Ser Ser Thr Thr Ala Tyr
65                  70                  75                  80

Met Gln Leu Arg Ser Leu Thr Ser Ala Asp Ser Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ala
            115

<210> SEQ ID NO 17
<211> LENGTH: 119
<212> TYPE: PRT
<213> ORGANISM: Mus sp.

<400> SEQUENCE: 17

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val His Trp Val Arg Gln Phe Pro Gly Lys Gly Leu Glu Trp Leu
        35                  40                  45

Gly Val Ile Trp Ser Asp Gly Ser Thr Asp Phe Asn Ala Pro Phe Lys
    50                  55                  60

Ser Arg Leu Ser Ile Asn Lys Asp Asn Ser Lys Ser Gln Val Phe Phe
65                  70                  75                  80

Lys Met Asn Ser Leu Gln Ile Asp Asp Thr Ala Ile Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ala
            115

<210> SEQ ID NO 18
<211> LENGTH: 119
<212> TYPE: PRT
<213> ORGANISM: Mus sp.

<400> SEQUENCE: 18

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val His Trp Val Arg Gln Phe Pro Gly Lys Gly Leu Glu Trp Leu
        35                  40                  45

Gly Val Ile Trp Ser Asp Gly Ser Thr Asp Tyr Asn Ala Pro Phe Lys
    50                  55                  60

Ser Arg Leu Ser Ile Asn Lys Asp Asn Ser Lys Ser Gln Val Phe Phe
65                  70                  75                  80

Lys Met Asn Ser Leu Gln Thr Asp Asp Thr Ala Ile Tyr Tyr Cys Ala
                85                  90                  95
```

```
Arg Lys Gly Gly Tyr Ser Gly Ser Trp Phe Ala Tyr Trp Gly Gln Gly
                100                 105                 110

Thr Leu Val Thr Val Ser Ala
        115
```

<210> SEQ ID NO 19
<211> LENGTH: 117
<212> TYPE: PRT
<213> ORGANISM: Mus sp.

<400> SEQUENCE: 19

```
Gln Val Gln Leu Lys Glu Ser Gly Pro Val Leu Val Ala Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Pro Pro Gly Lys Gly Leu Glu Trp Leu
            35                  40                  45

Gly Val Ile Trp Pro Val Gly Ser Thr Asn Tyr Asn Ser Ala Leu Met
        50                  55                  60

Ser Arg Leu Ser Ile His Lys Asp Asn Ser Lys Ser Gln Val Phe Leu
65                  70                  75                  80

Arg Met Asn Ser Leu Gln Thr Asp Asp Thr Ala Ile Tyr Tyr Cys Ala
                85                  90                  95

Lys Met Asp Trp Asp Asp Phe Phe Asp Tyr Trp Gly Gln Gly Thr Thr
                100                 105                 110

Leu Thr Val Ser Ser
        115
```

<210> SEQ ID NO 20
<211> LENGTH: 124
<212> TYPE: PRT
<213> ORGANISM: Mus sp.

<400> SEQUENCE: 20

```
Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Asp
                20                  25                  30

Tyr Ile His Trp Val Arg Gln Arg Pro Lys Gln Gly Leu Glu Trp Leu
            35                  40                  45

Gly Arg Ile Asp Pro Ala Asn Gly Asn Thr Lys Tyr Asp Pro Arg Phe
        50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Lys Ser Phe Pro Asp Asn Tyr Tyr Ser Tyr Asp Asp Ala Phe Ala
                100                 105                 110

Tyr Trp Gly Gln Gly Thr Leu Val Thr Val Ser Ala
        115                 120
```

<210> SEQ ID NO 21
<211> LENGTH: 12
<212> TYPE: PRT
<213> ORGANISM: Mus sp.

<400> SEQUENCE: 21

```
Thr Ala Ser Ser Ser Val Ser Ser Ser Tyr Leu His
```

```
<210> SEQ ID NO 22
<211> LENGTH: 11
<212> TYPE: PRT
<213> ORGANISM: Mus sp.

<400> SEQUENCE: 22

Leu Ala Ser Gln Thr Ile Gly Thr Trp Leu Ala
1               5                   10

<210> SEQ ID NO 23
<211> LENGTH: 11
<212> TYPE: PRT
<213> ORGANISM: Mus sp.

<400> SEQUENCE: 23

Leu Ala Ser Gln Thr Ile Gly Thr Trp Leu Gly
1               5                   10

<210> SEQ ID NO 24
<211> LENGTH: 16
<212> TYPE: PRT
<213> ORGANISM: Mus sp.

<400> SEQUENCE: 24

Arg Ser Ser Gln Asn Ile Val His Ser Asn Gly Asn Thr Tyr Leu Gln
1               5                   10                  15

<210> SEQ ID NO 25
<211> LENGTH: 11
<212> TYPE: PRT
<213> ORGANISM: Mus sp.

<400> SEQUENCE: 25

Arg Ala Ser Gln Asp Ile Tyr Lys Tyr Leu Asn
1               5                   10

<210> SEQ ID NO 26
<211> LENGTH: 12
<212> TYPE: PRT
<213> ORGANISM: Mus sp.

<400> SEQUENCE: 26

Thr Ala Ser Ser Ser Val Ser Ser Ser Tyr Phe His
1               5                   10

<210> SEQ ID NO 27
<211> LENGTH: 11
<212> TYPE: PRT
<213> ORGANISM: Mus sp.

<400> SEQUENCE: 27

Lys Ala Ser Gln Asp Val Gly Thr Asn Val Leu
1               5                   10

<210> SEQ ID NO 28
<211> LENGTH: 11
<212> TYPE: PRT
<213> ORGANISM: Mus sp.

<400> SEQUENCE: 28

Lys Ala Ser Gln Asn Val Gly Arg Ala Val Ala
1               5                   10
```

<210> SEQ ID NO 29
<211> LENGTH: 11
<212> TYPE: PRT
<213> ORGANISM: Mus sp.

<400> SEQUENCE: 29

Leu Ala Ser Gln Thr Ile Gly Thr Trp Leu Gly
1               5                   10

<210> SEQ ID NO 30
<211> LENGTH: 7
<212> TYPE: PRT
<213> ORGANISM: Mus sp.

<400> SEQUENCE: 30

Ser Thr Ser Asn Leu Ala Ser
1               5

<210> SEQ ID NO 31
<211> LENGTH: 7
<212> TYPE: PRT
<213> ORGANISM: Mus sp.

<400> SEQUENCE: 31

Ala Ala Thr Ser Leu Ala Asp
1               5

<210> SEQ ID NO 32
<211> LENGTH: 7
<212> TYPE: PRT
<213> ORGANISM: Mus sp.

<400> SEQUENCE: 32

Arg Ser Thr Thr Leu Ala Asp
1               5

<210> SEQ ID NO 33
<211> LENGTH: 7
<212> TYPE: PRT
<213> ORGANISM: Mus sp.

<400> SEQUENCE: 33

Lys Val Ser Asn Arg Phe Ser
1               5

<210> SEQ ID NO 34
<211> LENGTH: 7
<212> TYPE: PRT
<213> ORGANISM: Mus sp.

<400> SEQUENCE: 34

Tyr Thr Ser Gly Leu His Ser
1               5

<210> SEQ ID NO 35
<211> LENGTH: 7
<212> TYPE: PRT
<213> ORGANISM: Mus sp.

<400> SEQUENCE: 35

Arg Thr Ser Asn Leu Ala Ser
1               5

<210> SEQ ID NO 36

```
<211> LENGTH: 7
<212> TYPE: PRT
<213> ORGANISM: Mus sp.

<400> SEQUENCE: 36

Ser Ala Ser Tyr Arg His Ser
1               5

<210> SEQ ID NO 37
<211> LENGTH: 7
<212> TYPE: PRT
<213> ORGANISM: Mus sp.

<400> SEQUENCE: 37

Ser Ala Ser Asn Arg Tyr Thr
1               5

<210> SEQ ID NO 38
<211> LENGTH: 7
<212> TYPE: PRT
<213> ORGANISM: Mus sp.

<400> SEQUENCE: 38

Arg Ala Thr Ser Leu Ala Asp
1               5

<210> SEQ ID NO 39
<211> LENGTH: 9
<212> TYPE: PRT
<213> ORGANISM: Mus sp.

<400> SEQUENCE: 39

His Gln His His Arg Ser Pro Val Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Val Tyr Thr Thr Pro Leu Thr
1               5

<210> SEQ ID NO 41
<211> LENGTH: 9
<212> TYPE: PRT
<213> ORGANISM: Mus sp.

<400> SEQUENCE: 41

Gln Gln Leu Tyr Ser Ala Pro Tyr Thr
1               5

<210> SEQ ID NO 42
<211> LENGTH: 9
<212> TYPE: PRT
<213> ORGANISM: Mus sp.

<400> SEQUENCE: 42

Phe Gln Gly Ser His Val Pro Phe Thr
1               5
```

```
<210> SEQ ID NO 43
<211> LENGTH: 9
<212> TYPE: PRT
<213> ORGANISM: Mus sp.

<400> SEQUENCE: 43

Gln Gln Asp Ser Lys Phe Pro Trp Thr
1               5

<210> SEQ ID NO 44
<211> LENGTH: 9
<212> TYPE: PRT
<213> ORGANISM: Mus sp.

<400> SEQUENCE: 44

His Gln Phe His Arg Ser Pro Leu Thr
1               5

<210> SEQ ID NO 45
<211> LENGTH: 9
<212> TYPE: PRT
<213> ORGANISM: Mus sp.

<400> SEQUENCE: 45

Gln Gln Tyr Ser Arg Tyr Pro Leu Thr
1               5

<210> SEQ ID NO 46
<211> LENGTH: 9
<212> TYPE: PRT
<213> ORGANISM: Mus sp.

<400> SEQUENCE: 46

Gln Gln Tyr Ser Ser Tyr Pro Leu Thr
1               5

<210> SEQ ID NO 47
<211> LENGTH: 9
<212> TYPE: PRT
<213> ORGANISM: Mus sp.

<400> SEQUENCE: 47

Gln Gln Leu Tyr Ser Gly Pro Tyr Thr
1               5

<210> SEQ ID NO 48
<211> LENGTH: 10
<212> TYPE: PRT
<213> ORGANISM: Mus sp.

<400> SEQUENCE: 48

Gly Asn Thr Val Thr Ser Tyr Trp Met His
1               5                   10

<210> SEQ ID NO 49
<211> LENGTH: 10
<212> TYPE: PRT
<213> ORGANISM: Mus sp.

<400> SEQUENCE: 49

Gly Tyr Thr Phe Thr Asp Asn Tyr Met Asn
1               5                   10

<210> SEQ ID NO 50
<211> LENGTH: 10
```

```
<212> TYPE: PRT
<213> ORGANISM: Mus sp.

<400> SEQUENCE: 50

Gly Phe Asn Ile Lys Asp Asp Tyr Ile His
1               5                   10

<210> SEQ ID NO 51
<211> LENGTH: 10
<212> TYPE: PRT
<213> ORGANISM: Mus sp.

<400> SEQUENCE: 51

Gly Phe Ser Leu Thr Lys Phe Gly Val His
1               5                   10

<210> SEQ ID NO 52
<211> LENGTH: 10
<212> TYPE: PRT
<213> ORGANISM: Mus sp.

<400> SEQUENCE: 52

Gly Phe Ser Leu Ser Ser Tyr Glu Ile Asn
1               5                   10

<210> SEQ ID NO 53
<211> LENGTH: 10
<212> TYPE: PRT
<213> ORGANISM: Mus sp.

<400> SEQUENCE: 53

Gly Tyr Ser Phe Thr Ser Ser Trp Ile His
1               5                   10

<210> SEQ ID NO 54
<211> LENGTH: 10
<212> TYPE: PRT
<213> ORGANISM: Mus sp.

<400> SEQUENCE: 54

Gly Phe Ser Leu Thr Asn Tyr Ala Val His
1               5                   10

<210> SEQ ID NO 55
<211> LENGTH: 10
<212> TYPE: PRT
<213> ORGANISM: Mus sp.

<400> SEQUENCE: 55

Gly Phe Ser Leu Thr Asn Tyr Gly Val His
1               5                   10

<210> SEQ ID NO 56
<211> LENGTH: 10
<212> TYPE: PRT
<213> ORGANISM: Mus sp.

<400> SEQUENCE: 56

Gly Phe Asn Ile Lys Asp Asp Tyr Ile His
1               5                   10

<210> SEQ ID NO 57
<211> LENGTH: 17
<212> TYPE: PRT
<213> ORGANISM: Mus sp.
```

-continued

<400> SEQUENCE: 57

Glu Ile Leu Pro Ser Thr Gly Arg Thr Asn Tyr Asn Glu Asn Phe Lys
1               5                   10                  15

Gly

<210> SEQ ID NO 58
<211> LENGTH: 17
<212> TYPE: PRT
<213> ORGANISM: Mus sp.

<400> SEQUENCE: 58

Arg Val Asn Pro Ser Asn Gly Asp Thr Lys Tyr Asn Gln Asn Phe Lys
1               5                   10                  15

Gly

<210> SEQ ID NO 59
<211> LENGTH: 17
<212> TYPE: PRT
<213> ORGANISM: Mus sp.

<400> SEQUENCE: 59

Arg Ile Asp Pro Ala Asn Gly Asn Thr Lys Tyr Ala Pro Lys Phe Gln
1               5                   10                  15

Asp

<210> SEQ ID NO 60
<211> LENGTH: 16
<212> TYPE: PRT
<213> ORGANISM: Mus sp.

<400> SEQUENCE: 60

Val Ile Trp Ala Gly Gly Pro Thr Asn Tyr Asn Ser Ala Leu Met Ser
1               5                   10                  15

<210> SEQ ID NO 61
<211> LENGTH: 16
<212> TYPE: PRT
<213> ORGANISM: Mus sp.

<400> SEQUENCE: 61

Val Ile Trp Thr Gly Ile Thr Thr Asn Tyr Asn Ser Ala Leu Ile Ser
1               5                   10                  15

<210> SEQ ID NO 62
<211> LENGTH: 15
<212> TYPE: PRT
<213> ORGANISM: Mus sp.

<400> SEQUENCE: 62

Glu Ile Asn Pro Gly Asn Val Arg Thr Asn Tyr Asn Glu Asn Phe
1               5                   10                  15

<210> SEQ ID NO 63
<211> LENGTH: 16
<212> TYPE: PRT
<213> ORGANISM: Mus sp.

<400> SEQUENCE: 63

Val Ile Trp Ser Asp Gly Ser Thr Asp Phe Asn Ala Pro Phe Lys Ser
1               5                   10                  15

```
<210> SEQ ID NO 64
<211> LENGTH: 16
<212> TYPE: PRT
<213> ORGANISM: Mus sp.

<400> SEQUENCE: 64

Val Ile Trp Ser Asp Gly Ser Thr Asp Tyr Asn Ala Pro Phe Lys Ser
1               5                   10                  15

<210> SEQ ID NO 65
<211> LENGTH: 16
<212> TYPE: PRT
<213> ORGANISM: Mus sp.

<400> SEQUENCE: 65

Val Ile Trp Pro Val Gly Ser Thr Asn Tyr Asn Ser Ala Leu Met Ser
1               5                   10                  15

<210> SEQ ID NO 66
<211> LENGTH: 17
<212> TYPE: PRT
<213> ORGANISM: Mus sp.

<400> SEQUENCE: 66

Arg Ile Asp Pro Ala Asn Gly Asn Thr Lys Tyr Asp Pro Arg Phe Gln
1               5                   10                  15

Asp

<210> SEQ ID NO 67
<211> LENGTH: 10
<212> TYPE: PRT
<213> ORGANISM: Mus sp.

<400> SEQUENCE: 67

Val Tyr Phe Gly Asn Pro Trp Phe Ala Tyr
1               5                   10

<210> SEQ ID NO 68
<211> LENGTH: 16
<212> TYPE: PRT
<213> ORGANISM: Mus sp.

<400> SEQUENCE: 68

Thr Lys Asn Phe Tyr Ser Ser Tyr Ser Tyr Asp Asp Ala Met Asp Tyr
1               5                   10                  15

<210> SEQ ID NO 69
<211> LENGTH: 15
<212> TYPE: PRT
<213> ORGANISM: Mus sp.

<400> SEQUENCE: 69

Ser Phe Pro Asn Asn Tyr Tyr Ser Tyr Asp Asp Ala Phe Ala Tyr
1               5                   10                  15

<210> SEQ ID NO 70
<211> LENGTH: 10
<212> TYPE: PRT
<213> ORGANISM: Mus sp.

<400> SEQUENCE: 70

Gln Ile Tyr Tyr Ser Thr Leu Val Asp Tyr
1               5                   10
```

```
<210> SEQ ID NO 71
<211> LENGTH: 12
<212> TYPE: PRT
<213> ORGANISM: Mus sp.

<400> SEQUENCE: 71

Gly Thr Gly Thr Gly Phe Tyr Tyr Ala Met Asp Tyr
1               5                   10

<210> SEQ ID NO 72
<211> LENGTH: 10
<212> TYPE: PRT
<213> ORGANISM: Mus sp.

<400> SEQUENCE: 72

Val Phe Tyr Gly Glu Pro Tyr Phe Pro Tyr
1               5                   10

<210> SEQ ID NO 73
<211> LENGTH: 11
<212> TYPE: PRT
<213> ORGANISM: Mus sp.

<400> SEQUENCE: 73

Lys Gly Gly Tyr Ser Gly Ser Trp Phe Ala Tyr
1               5                   10

<210> SEQ ID NO 74
<211> LENGTH: 9
<212> TYPE: PRT
<213> ORGANISM: Mus sp.

<400> SEQUENCE: 74

Met Asp Trp Asp Asp Phe Phe Asp Tyr
1               5

<210> SEQ ID NO 75
<211> LENGTH: 15
<212> TYPE: PRT
<213> ORGANISM: Mus sp.

<400> SEQUENCE: 75

Ser Phe Pro Asp Asn Tyr Tyr Ser Tyr Asp Asp Ala Phe Ala Tyr
1               5                   10                  15

<210> SEQ ID NO 76
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Thr Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 77
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Ile Leu Ala Ser Gly Val Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 78
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Trp
            35                  40                  45

Ile Tyr Arg Thr Ser Arg Leu Ala Ser Gly Val Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 79
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 79

Glu Ile Val Leu Thr Gln Ser Pro Gly Thr Leu Ser Leu Ser Pro Gly
1               5                   10                  15

Glu Arg Ala Thr Met Thr Cys Thr Ala Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Arg Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Phe His Arg Ser Pro
                85                  90                  95

Leu Thr Phe Gly Gln Gly Thr Lys Leu Glu Ile Lys
                100                 105

<210> SEQ ID NO 80
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Val Ser Ser Ser
            20                  25                  30

Tyr Phe His Trp Tyr Gln Gln Lys Pro Gly Gln Ala Pro Arg Leu Trp
        35                  40                  45

Ile Tyr Arg Thr Ser Arg Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Ala Gly Thr Lys Leu Glu Ile Lys
                100                 105

<210> SEQ ID NO 81
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Ile Val Leu Thr Gln Ser Pro Gly Thr Leu Ser Leu Ser Pro Gly
1               5                   10                  15

Glu Arg Val Thr Met Ser Cys Thr Ala Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Gln Leu Ala Ser Gly Ile Pro Asp Arg Phe Ser
50                  55                  60

```
Gly Ser Gly Ser Gly Thr Asp Phe Thr Leu Thr Ile Ser Arg Leu Glu
 65                  70                  75                  80

Pro Glu Asp Ala Ala Thr Tyr Tyr Cys His Gln Phe His Arg Ser Pro
                 85                  90                  95

Leu Thr Phe Gly Gln Gly Thr Lys Leu Glu Ile Lys
            100                 105

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Ile Val Leu Thr Gln Ser Pro Gly Thr Leu Ser Leu Ser Pro Gly
 1               5                  10                  15

Glu Arg Ala Thr Met Thr Cys Thr Ala Ser Ser Ser Val Ser Ser Ser
                 20                  25                  30

Tyr Phe His Trp Tyr Gln Gln Lys Pro Gly Gln Ala Pro Arg Leu Leu
             35                  40                  45

Ile Tyr Arg Thr Ser Lys Leu Ala Ser Gly Val Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Thr Tyr Tyr Cys His Gln Phe His Arg Ser Pro
                 85                  90                  95

Leu Thr Phe Gly Gln Gly Thr Lys Leu Glu Ile Lys
            100                 105

<210> SEQ ID NO 83
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Ile Val Leu Thr Gln Ser Pro Gly Thr Leu Ser Leu Ser Pro Gly
 1               5                  10                  15

Glu Arg Ala Thr Met Ser Cys Thr Ala Ser Ser Ser Val Ser Ser Ser
                 20                  25                  30

Tyr Phe His Trp Tyr Gln Gln Lys Pro Gly Gln Ala Pro Arg Leu Leu
             35                  40                  45

Ile Tyr Arg Thr Ser His Leu Ala Ser Gly Ile Pro Gly Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Ala Ala Val Tyr Tyr Cys His Gln Phe His Arg Ser Pro
                 85                  90                  95

Leu Thr Phe Gly Gln Gly Thr Lys Leu Glu Ile Lys
            100                 105

<210> SEQ ID NO 84
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 84

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Glu Tyr Phe Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Ala Arg Phe Ser Gly

```
                     50                  55                  60
Ser Gly Ser Gly Thr Glu Phe Thr Leu Thr Ile Ser Ser Leu Gln Ser
 65                  70                  75                  80

Glu Asp Phe Ala Glu Tyr Tyr Cys Gln Gln Tyr Ser Arg Tyr Pro Leu
                 85                  90                  95

Thr Phe Gly Gln Gly Thr Lys Leu Glu Ile Lys
            100                 105
```

<210> SEQ ID NO 87
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Ser Phe Thr Ser Ser
                20                  25                  30

Trp Ile His Trp Val Arg Gln Ala Pro Gly Gln Gly Leu Glu Trp Ile
            35                  40                  45

Gly Glu Ile Asn Pro Gly Asn Val Arg Thr Asn Tyr Asn Glu Asn Phe
        50                  55                  60

Arg Asn Lys Ala Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Val Val Phe Tyr Gly Glu Pro Tyr Phe Pro Tyr Trp Gly Gln Gly
            100                 105                 110

Thr Leu Val Thr Val Ser Ser
        115
```

<210> SEQ ID NO 88
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Ser Phe Thr Ser Ser
                20                  25                  30

Trp Ile His Trp Val Arg Gln Arg Pro Gly Gln Gly Leu Glu Trp Ile
            35                  40                  45

Gly Glu Ile Asn Pro Gly Asn Val Arg Thr Asn Tyr Asn Glu Asn Phe
        50                  55                  60

Arg Asn Arg Val Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Val Val Phe Tyr Gly Glu Pro Tyr Phe Pro Tyr Trp Gly Gln Gly
            100                 105                 110

Thr Leu Val Thr Val Ser Ser
```

<210> SEQ ID NO 89
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Met
        35                  40                  45

Gly Glu Ile Asn Pro Gly Asn Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 90
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Met
        35                  40                  45

Gly Glu Ile Asn Pro Gly Asn Val Arg Thr Asn Tyr Asn Glu Asn Phe
    50                  55                  60

Arg Asn Arg Ala Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 91
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Met
        35                  40                  45

Gly Glu Ile Leu Pro Gly Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 92
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Ile
        35                  40                  45

Gly Glu Ile Asn Pro Gly Ala Val Arg Thr Asn Tyr Asn Glu Asn Phe
    50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 93
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
            35                  40                  45

Gly Glu Ile Asn Pro Gly Leu Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
                100                 105                 110

Thr Leu Val Thr Val Ser Ser
        115

<210> SEQ ID NO 94
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
            35                  40                  45

Gly Glu Ile Asn Pro Gly Ala Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
                100                 105                 110

Thr Leu Val Thr Val Ser Ser
        115

<210> SEQ ID NO 95
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
            35                  40                  45

Gly Glu Ile Asn Pro Gly Ser Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 96
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Asn Lys Asp Thr Ser Lys Ser Gln Val Ser Phe
65                  70                  75                  80

Lys Met Ser Ser Val Gln Ala Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Thr Ser Lys Asn Gln Val Ser Leu
65                  70                  75                  80

Lys Met Asn Ser Leu Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 98
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Leu
65                  70                  75                  80

Lys Met Asn Ser Val Thr Val Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 99
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Val Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Val Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 100
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Gln Val Gln Leu Gln Glu Ser Gly Pro Gly Leu Val Ala Pro Ser Glu
1               5                   10                  15

Thr Leu Ser Leu Thr Cys Thr Val Ser Gly Phe Ser Leu Thr Asp Tyr
            20                  25                  30

Ala Val His Trp Ile Arg Gln Phe Pro Gly Lys Gly Leu Glu Trp Ile
        35                  40                  45

Gly Val Ile Trp Ser Asp Gly Ser Thr Asp Phe Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115
```

<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

```
Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Phe
65                  70                  75                  80

Lys Met Ser Ser Val Thr Ala Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115
```

<210> SEQ ID NO 102
<211> LENGTH: 7
<212> TYPE: PRT
<213> ORGANISM: Mus sp.

<400> SEQUENCE: 102

```
Arg Thr Ser Thr Leu Ala Ser
1               5
```

<210> SEQ ID NO 103
<211> LENGTH: 7
<212> TYPE: PRT
<213> ORGANISM: Mus sp.

-continued

<400> SEQUENCE: 103

Arg Thr Ser Ile Leu Ala Ser
1               5

<210> SEQ ID NO 104
<211> LENGTH: 7
<212> TYPE: PRT
<213> ORGANISM: Mus sp.

<400> SEQUENCE: 104

Arg Thr Ser Arg Leu Ala Ser
1               5

<210> SEQ ID NO 105
<211> LENGTH: 7
<212> TYPE: PRT
<213> ORGANISM: Mus sp.

<400> SEQUENCE: 105

Arg Thr Ser Gln Leu Ala Ser
1               5

<210> SEQ ID NO 106
<211> LENGTH: 7
<212> TYPE: PRT
<213> ORGANISM: Mus sp.

<400> SEQUENCE: 106

Arg Thr Ser Lys Leu Ala Ser
1               5

<210> SEQ ID NO 107
<211> LENGTH: 10
<212> TYPE: PRT
<213> ORGANISM: Mus sp.

<400> SEQUENCE: 107

Gly Phe Ser Leu Thr Asp Tyr Ala Val His
1               5                   10

<210> SEQ ID NO 108
<211> LENGTH: 15
<212> TYPE: PRT
<213> ORGANISM: Mus sp.

<400> SEQUENCE: 108

Glu Ile Leu Pro Gly Val Val Arg Thr Asn Tyr Asn Glu Asn Phe
1               5                   10                  15

<210> SEQ ID NO 109
<211> LENGTH: 15
<212> TYPE: PRT
<213> ORGANISM: Mus sp.

<400> SEQUENCE: 109

Glu Ile Asn Pro Gly Ala Val Arg Thr Asn Tyr Asn Glu Asn Phe
1               5                   10                  15

<210> SEQ ID NO 110
<211> LENGTH: 15
<212> TYPE: PRT
<213> ORGANISM: Mus sp.

<400> SEQUENCE: 110

Glu Ile Asn Pro Gly Leu Val Arg Thr Asn Tyr Asn Glu Asn Phe
1               5                   10                  15

<210> SEQ ID NO 111
<211> LENGTH: 15
<212> TYPE: PRT
<213> ORGANISM: Mus sp.

<400> SEQUENCE: 111

Glu Ile Asn Pro Gly Ser Val Arg Thr Asn Tyr Asn Glu Asn Phe
1               5                   10                  15

<210> SEQ ID NO 112
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

```
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 114
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Thr Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 115
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Ile Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 116
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116
```

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Trp
        35                  40                  45

Ile Tyr Arg Thr Ser Arg Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 117
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Arg Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 118
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30

Tyr Phe His Trp Tyr Gln Lys Pro Gly Gln Ala Pro Arg Leu Trp
        35                  40                  45

Ile Tyr Arg Thr Ser Arg Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Ala Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 119
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Gln Ile Val Leu Thr Gln Ser Pro Gly Thr Leu Ser Leu Ser Pro Gly
1               5                   10                  15

Glu Arg Val Thr Met Ser Cys Thr Ala Ser Ser Val Ser Ser Ser
            20                  25                  30

Tyr Phe His Trp Tyr Gln Gln Lys Pro Gly Gln Ala Pro Arg Leu Leu
            35                  40                  45

Ile Tyr Arg Thr Ser Gln Leu Ala Ser Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
            210                 215

<210> SEQ ID NO 120
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Val Ser Ser Ser
            20                  25                  30

Tyr Phe His Trp Tyr Gln Gln Lys Pro Gly Gln Ala Pro Arg Leu Leu
            35                  40                  45

Ile Tyr Arg Thr Ser Lys Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
```

```
                    130                 135                 140
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 121
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser His Leu Ala Ser Gly Ile Pro Gly Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Val Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 122
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 122

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Glu Tyr Phe Cys Gln Gln Tyr Ser Arg Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 123
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Arg Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 124
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Glu Tyr Tyr Cys Gln Gln Tyr Ser Arg Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 125
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Asn Val Arg Thr Asn Tyr Asn Glu Asn Phe
50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
```

―continued

```
                    405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 126
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
              305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 127
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Lys Gln Ala Pro Gly Gln Gly Leu Glu Trp Met
            35                  40                  45

Gly Glu Ile Asn Pro Gly Asn Val Arg Thr Asn Tyr Asn Glu Asn Phe
        50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
```

```
                210               215                220
Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 128
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Arg Pro Gly Gln Gly Leu Glu Trp Met
            35                  40                  45

Gly Glu Ile Asn Pro Gly Asn Val Arg Thr Asn Tyr Asn Glu Asn Phe
        50                  55                  60

Arg Asn Arg Ala Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 129
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
```

```
                20                  25                  30
Trp Ile His Trp Val Arg Gln Arg Pro Gly Gln Gly Leu Glu Trp Met
            35                  40                  45
Gly Glu Ile Leu Pro Gly Val Val Arg Thr Asn Tyr Asn Glu Asn Phe
        50                  55                  60
Arg Asn Lys Val Thr Met Thr Val Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Thr Val Val Phe Tyr Gly Glu Pro Tyr Phe Pro Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

Lys

<210> SEQ ID NO 130
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Ile
        35                  40                  45

Gly Glu Ile Asn Pro Gly Ala Val Arg Thr Asn Tyr Asn Glu Asn Phe
    50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 131
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Leu Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 132
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ala Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

-continued

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 133
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ser Val Arg Thr Asn Tyr Asn Glu Asn Phe
    50                  55                  60
```

Arg Asn Lys Ala Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 134
<211> LENGTH: 449
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 134

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Asn Lys Asp Thr Ser Lys Ser Gln Val Ser Phe
65                  70                  75                  80

Lys Met Ser Ser Val Gln Ala Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 135
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Thr Ser Lys Asn Gln Val Ser Leu
65                  70                  75                  80

Lys Met Asn Ser Leu Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```

```
<210> SEQ ID NO 136
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Leu
65                  70                  75                  80

Lys Met Asn Ser Val Thr Ala Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 137
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Val Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Val Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 138
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Gln Glu Ser Gly Pro Gly Leu Val Ala Pro Ser Glu
1               5                   10                  15

Thr Leu Ser Leu Thr Cys Thr Val Ser Gly Phe Ser Leu Thr Asp Tyr
            20                  25                  30

Ala Val His Trp Ile Arg Gln Phe Pro Gly Lys Gly Leu Glu Trp Ile
        35                  40                  45

Gly Val Ile Trp Ser Asp Gly Ser Thr Asp Phe Asn Ala Pro Phe Lys
50                  55                  60

Ser Arg Val Thr Ile Ser Lys Asp Thr Ser Lys Asn Gln Val Ser Phe
65                  70                  75                  80

Lys Leu Ser Ser Val Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu

```
                420                 425                 430
Ala Leu His Asn His Tyr Thr Gln Lys Ser Leu Ser Leu Ser Pro Gly
            435                 440                 445

Lys

<210> SEQ ID NO 139
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Phe
65                  70                  75                  80

Lys Met Ser Ser Val Thr Ala Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                            325                 330                 335
Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 140
<211> LENGTH: 7
<212> TYPE: PRT
<213> ORGANISM: Mus sp.

<400> SEQUENCE: 140

Arg Thr Ser His Leu Ala Ser
1               5

<210> SEQ ID NO 141
<211> LENGTH: 5
<212> TYPE: PRT
<213> ORGANISM: Mus sp.

<400> SEQUENCE: 141

Ser Ser Trp Ile His
1               5

<210> SEQ ID NO 142
<211> LENGTH: 17
<212> TYPE: PRT
<213> ORGANISM: Mus sp.

<400> SEQUENCE: 142

Glu Ile Asn Pro Gly Asn Val Arg Thr Asn Tyr Asn Glu Asn Phe Arg
1               5                   10                  15

Asn
```

ANTI-IL-36R ANTIBODIES FOR THE TREATMENT OF PYODERMA GANGRENOSUM

SEQUENCE LISTING

The instant application contains a Sequence Listing which has been submitted in ASCII format via EFS-Web and is hereby incorporated by reference in its entirety. Said ASCII copy, created on Sep. 16, 2021, is named 09-705-US-2_SL.txt and is 146,422 bytes in size.

TECHNICAL FIELD OF THE INVENTION

The present invention relates to the administration of an anti-interleukin-36 receptor (anit-IL-36R) antibody to a subject with a neutrophilic dermatosis (ND) such as hidradenitis suppurativa (HS) or subcorneal pustulosis (Sneddon-Wilkinson) and the treatment and/or prevention of the neutrophilic dermatosis in the subject. More specifically, the invention relates to the administration of spesolimab to a subject suffering from a neutrophilic dermatosis.

BACKGROUND

Neutrophilic dermatoses are a heterogeneous group of inflammatory skin disorders that present with unique clinical features but are unified by the presence of a sterile, predominantly neutrophilic infiltrate on histopathology. The morphology of cutaneous lesions associated with these disorders is heterogeneous, which renders diagnosis challenging. Moreover, a thorough evaluation is required to exclude diseases that mimic these disorders and to diagnose potential associated infectious, inflammatory, and neoplastic processes. While some neutrophilic dermatoses may resolve spontaneously, most require treatment to achieve remission. Delays in diagnosis and treatment can lead to significant patient morbidity and even mortality.

A neutrophilic dermatosis may be seen in isolation or more than one type may occur in the same individual. Neutrophilic dermatoses include hidradenitis suppurativa (HS); acute generalized exanthematous pustulosis; acute febrile neutrophilic dermatosis (Sweet syndrome); amicrobial pustulosis of the folds (APF); Behcet disease; Bowel bypass syndrome (bowel-associated dermatitis-arthritis syndrome); bowel-associated dermatosis-arthritis syndrome (BADAS).

Typical treatments include corticosteroids, topical lotions and moisturizers, antibiotics, anti-viral and anti-fungal agents. Most treatment options, however, offer only temporary, incomplete, symptom relief. Thus, a need exists in the art for novel targeted therapies for the treatment and/or prevention of neutrophilic dermatoses.

SUMMARY OF THE INVENTION

The present invention addresses the above need by providing bio-therapeutics, in particular antibodies, which bind to IL-36R as a first-second-, third- or subsequent-line therapy for treating neutrophilic dermatoses.

In one aspect, the present invention relates to a method for treating, preventing or ameliorating a neutrophilic dermatosis (ND) in a subject, comprising administering to the subject a therapeutically effective amount of an anti-IL-36R antibody or an antigen-binding fragment thereof (as disclosed herein). In an embodiment relating to this aspect, the anti-IL-36R antibody is spesolimab.

In one aspect, the present invention relates to a method of treating a skin disorder associated with neutrophilic dermatoses in a patient, said method(s) including administering or having administered to the patient a therapeutically effective amount of an anti-IL-36R antibody of the present invention or an antigen binding fragment thereof (as disclosed herein). In an embodiment relating to this aspect, the anti-IL-36R antibody is spesolimab.

In one aspect, the present invention relates to a method of treating skin inflammation associated with neutrophilic dermatoses in a subject, said method including administering or having administered to the subject a therapeutically effective amount of an anti-IL-36R antibody of the present invention or an antigen binding fragment thereof (as disclosed herein). In an embodiment relating to this aspect, the anti-IL-36R antibody is spesolimab.

In one aspect, the present invention relates to a method preventing or reducing neutrophilic infiltrates in affected skin tissues in a subject suffering from a neutrophilic dermatosis, said method including administering or having administered to the subject a therapeutically effective amount of an anti-IL-36R antibody of the present invention or an antigen binding fragment thereof. In an embodiment relating to this aspect, the anti-IL-36R antibody is spesolimab.

In one aspect, the present invention relates to a method of reducing microbial colonization of the skin in a subject with neutrophilic dermatosis comprising administering to the subject a therapeutically effective amount of an anti-IL-36R antibody or an antigen-binding fragment thereof, as disclosed herein. In an embodiment relating to this aspect, the colonization is of a microbe selected from the group consisting of *Staphylococcus aureus, Streptococcus* spp., *Pseudomonas aeruginosa, Bacteroides* spp., molluscum contagiosum virus, Herpes simplex virus, coxsackievirus, vaccinia virus, *Candida albicans, Microsporum* spp., *Trichophyton* spp., *Penicillium* spp., *Cladosporium* spp., *Alternaria* spp., and *Aspergillus* spp. In another embodiment relating to this aspect, the microbe is *Staphylococcus aureus* (*S. aureus*). In another embodiment relating to this aspect, the *S. aureus* colonization is reduced by at least 10% or by at least 20% from the baseline following the administration of the anti-IL-36R antibody or an antigen-binding fragment thereof, as disclosed herein. In an embodiment relating to this aspect, the anti-IL-36R antibody is spesolimab.

In one aspect, the present invention relates to a method of reducing susceptibility to a skin infection in a subject with neutrophilic dermatosis comprising administering to the subject a therapeutically effective amount of an anti-IL-36-R antibody or an antigen-binding fragment thereof (as disclosed herein). In an embodiment relating to this aspect, the skin infection is caused by a microbe selected from the group consisting of *Staphylococcus aureus, Streptococcus* spp., *Pseudomonas aeruginosa, Bacteroides* spp., Herpes simplex virus, molluscum contagiosum virus, coxsackievirus, vaccinia virus, *Candida albicans, Microsporum* spp., *Trichophyton* spp., *Penicillium* spp., *Cladosporium* spp., *Alternaria* spp., and *Aspergillus* spp. In another embodiment relating to this aspect, the microbe is *Staphylococcus aureus* (*S. aureus*). In an embodiment relating to this aspect, the anti-IL-36R antibody is spesolimab.

In an embodiment relating to any of the above aspects, a second therapeutic agent is administered to the subject before, after, or concurrent with the anti-IL-36R antibody or an antigen-binding fragment thereof. In a related embodiment, the second therapeutic agent is selected from the group consisting of an anti-bacterial agent, an anti-viral agent, an anti-fungal agent, another IL-36R antagonist, an IgE inhibitor, a corticosteroid, NSAID, an IL-4R antagonist, and IFNγ.

In an embodiment relating to any of the above aspects, the anti-IL-36R antibody includes: a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 53 or 141 (H-CDR1); the amino acid sequence of SEQ ID NO: 62, 108, 109, 110, 111 or 142 (H-CDR2); the amino acid sequence of SEQ ID NO: 72 (H-CDR3).

In an embodiment relating to any of the above aspects, the anti-IL-36R antibody includes: a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 141 (H-CDR1); the amino acid sequence of SEQ ID NO: 62, 108, 109, 110, 111 or 142 (H-CDR2); the amino acid sequence of SEQ ID NO: 72 (H-CDR3).

In an embodiment relating to any of the above aspects, the anti-IL-36R antibody includes:

I. a) a light chain variable region comprising the amino acid sequence of SEQ ID NO: 26 (L-CDR1); the amino acid sequence of SEQ ID NO: 102 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or II. a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or III. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or IV. a) a light chain variable region comprising the amino acid sequence of SEQ ID NO: 26 (L-CDR1); the amino acid sequence of SEQ ID NO: 105 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or V. a) a light chain variable region comprising the amino acid sequence of SEQ ID NO: 26 (L-CDR1); the amino acid sequence of SEQ ID NO: 106 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VI. a) a light chain variable region comprising the amino acid sequence of SEQ ID NO: 26 (L-CDR1); the amino acid sequence of SEQ ID NO: 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VII. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 141 (H-CDR1); the amino acid sequence of SEQ ID NO: 62, 108, 109, 110, 111 or 142 (H-CDR2); the amino acid sequence of SEQ ID NO: 72 (H-CDR3).

In an embodiment relating to any of the above aspects, the anti-IL-36R antibody includes:

(i) a light chain variable region comprising the amino acid sequence of SEQ ID NO: 77; and a heavy chain variable region comprising the amino acid sequence of SEQ ID NO: 87; or (ii) a light chain variable region comprising the amino acid sequence of SEQ ID NO: 77; and a heavy chain variable region comprising the amino acid sequence of SEQ ID NO: 88; or (iii) a light chain variable region comprising the amino acid sequence of SEQ ID NO: 77; and a heavy chain variable region comprising the amino acid sequence of SEQ ID NO: 89; or (iv) a light chain variable region comprising the amino acid sequence of SEQ ID NO: 80; and a heavy chain variable region comprising the amino acid sequence of SEQ ID NO: 87; or (v) a light chain variable region comprising the amino acid sequence of SEQ ID NO: 80; and a heavy chain variable region comprising the amino acid sequence of SEQ ID NO: 88; or (vi) a light chain variable region comprising the amino acid sequence of SEQ ID NO: 80; and a heavy chain variable region comprising the amino acid sequence of SEQ ID NO: 89; or (vii) a light chain variable region comprising the amino acid sequence of SEQ ID NO: 85; and a heavy chain variable region comprising the amino acid sequence of SEQ ID NO: 100; or (viii) a light chain variable region comprising the amino acid sequence of SEQ ID NO: 85; and a heavy chain variable region comprising the amino acid sequence of SEQ ID NO:101; or (ix) a light chain variable region comprising the amino acid sequence of SEQ ID NO: 86; and a heavy chain variable region comprising the amino acid sequence of SEQ ID NO: 100; or (x) a light chain variable region comprising the amino acid sequence of SEQ ID NO: 86; and a heavy chain variable region comprising the amino acid sequence of SEQ ID NO:101.

In an embodiment relating to any of the above aspects, the anti-IL-36R antibody includes:

i. a light chain comprising the amino acid sequence of SEQ ID NO: 115; and a heavy chain comprising the amino acid sequence of SEQ ID NO: 125; or
ii. a light chain comprising the amino acid sequence of SEQ ID NO: 115; and a heavy chain comprising the amino acid sequence of SEQ ID NO: 126; or
iii. a light chain comprising the amino acid sequence of SEQ ID NO: 115; and a heavy chain comprising the amino acid sequence of SEQ ID NO: 127; or
iv. a light chain comprising the amino acid sequence of SEQ ID NO: 118; and a heavy chain comprising the amino acid sequence of SEQ ID NO: 125; or
v. a light chain comprising the amino acid sequence of SEQ ID NO: 118; and a heavy chain comprising the amino acid sequence of SEQ ID NO: 126; or
vi. a light chain comprising the amino acid sequence of SEQ ID NO: 118; and a heavy chain comprising the amino acid sequence of SEQ ID NO: 127; or
vii. a light chain comprising the amino acid sequence of SEQ ID NO: 123; and a heavy chain comprising the amino acid sequence of SEQ ID NO: 138; or
viii. a light chain comprising the amino acid sequence of SEQ ID NO: 123; and a heavy chain comprising the amino acid sequence of SEQ ID NO: 139; or
ix. a light chain comprising the amino acid sequence of SEQ ID NO: 124; and a heavy chain comprising the amino acid sequence of SEQ ID NO: 138.

In an embodiment relating to any of the above aspects and embodiments, the neutrophilic dermatosis is selected from the group consisting of hidradenitis suppurativa (HS); acute generalized exanthematous pustulosis; acute febrile neutrophilic dermatosis (Sweet syndrome); amicrobial pustulosis of the folds (APF); Behcet disease; Bowel bypass syndrome (bowel-associated dermatitis-arthritis syndrome); bowel-associated dermatosis-arthritis syndrome (BADAS); CARD14-mediated pustular psoriasis (CAMPS); cryopyrin associated periodic syndromes (CAPS); deficiency of interleukin-36 receptor antagonist (DITRA); deficiency of interleukin-I receptor antagonist (DIRA); erythema elevatum diutinum; Histiocytoid neutrophilic dermatitis; infantile acropustulosis; neutrophilic dermatosis of the dorsal hands; neutrophilic eccrine hidradenitis; neutrophilic urticarial dermatosis; palisading neutrophilic granulomatous dermatitis; plaque psoriasis; pyoderma gangrenosum, acne, and hidradenitis suppurativa (PASH) syndrome; pyoderma gangrenosum (PG); pyoderma gangrenosum and acne (PAPA); pyogenic arthritis; skin lesions of Behcet's disease; Still's disease; subcorneal pustulosis (Sneddon-Wilkinson); synovitis, acne, pustulosis-hyperostosis; ostcitis (SAPHO) syndrome; rheumatoid neutrophilic dermatitis (RND), and ichthyosis (and its subtypes including netherton syndrome or NS).

In a related embodiment, the neutrophilic dermatosis is hidradenitis suppurativa (HS). In a related embodiment, the neutrophilic dermatosis is acute generalized exanthematous pustulosis. In a related embodiment, the neutrophilic dermatosis is acute febrile neutrophilic dermatosis (Sweet syndrome). In a related embodiment, the neutrophilic dermatosis is amicrobial pustulosis of the folds (APF). In a related embodiment, the neutrophilic dermatosis is Behcet disease. In a related embodiment, the neutrophilic dermatosis is bowel bypass syndrome (bowel-associated dermatitis-arthritis syndrome). In a related embodiment, the neutrophilic dermatosis is bowel-associated dermatosis-arthritis syndrome (BADAS). In a related embodiment, the neutrophilic dermatosis is CARD14-mediated pustular psoriasis (CAMPS). In a related embodiment, the neutrophilic dermatosis is cryopyrin associated periodic syndromes (CAPS). In a related embodiment, the neutrophilic dermatosis is deficiency of interleukin-36 receptor antagonist (DITRA). In a related embodiment, the neutrophilic dermatosis is deficiency of interleukin-I receptor antagonist (DIRA). In a related embodiment, the neutrophilic dermatosis is erythema elevatum diutinum. In a related embodiment, the neutrophilic dermatosis is Histiocytoid neutrophilic dermatitis. In a related embodiment, the neutrophilic dermatosis is infantile acropustulosis. In a related embodiment, the neutrophilic dermatosis is neutrophilic dermatosis of the dorsal hands. In a related embodiment, the neutrophilic dermatosis is neutrophilic eccrine hidradenitis. In a related embodiment, the neutrophilic dermatosis is neutrophilic urticarial dermatosis. In a related embodiment, the neutrophilic dermatosis is palisading neutrophilic granulomatous dermatitis. In a related embodiment, the neutrophilic dermatosis is plaque psoriasis. In a related embodiment, the neutrophilic dermatosis is pyoderma gangrenosum, acne, and hidradenitis suppurativa (PASH) syndrome. In a related embodiment, the neutrophilic dermatosis is pyoderma gangrenosum (PG). In a related embodiment, the neutrophilic dermatosis is pyoderma gangrenosum and acne (PAPA). In a related embodiment, the neutrophilic dermatosis is pyogenic arthritis. In a related embodiment, the neutrophilic dermatosis is skin lesions of Behcet's disease. In a related embodiment, the neutrophilic dermatosis is Still's disease. In a related embodiment, the neutrophilic dermatosis is subcorneal pustulosis (Sneddon-Wilkinson). In a related embodiment, the neutrophilic dermatosis is synovitis, acne, pustulosis-hyperostosis and ostcitis (SAPHO) syndrome. In a related embodiment, the neutrophilic dermatosis is rheumatoid neutrophilic dermatitis (RND). In a related embodiment, the neutrophilic dermatosis is ichthyosis (and its subtypes including netherton syndrome or NS).

In another embodiment relating to any of the above aspects and embodiments described herein, the anti-IL-36R antibody is administered in the range of about 0.001 to about 1000 mg to a subject suffering from a neutrophilic dermatosis.

It will be understood that any of the herein disclosed methods, administration schemes and/or dosing regimens also equally apply to the use of any of the disclosed anti-IL-36R antibodies in such methods, administration schemes and/or dosing regimens: i.e. an anti-IL-36R antibody, as disclosed herein, for use in the treatment, prevention, reducing and/or amelioration of any of the disclosed diseases and/or conditions. In other words, the invention also provides for the use of an anti-IL-36R antibody, as disclosed herein, for the manufacture of a medicament for the treatment, prevention, reducing and/or amelioration of any of the disclosed diseases and/or conditions.

Additional features and advantages of the present invention will-become apparent from a review of the ensuing detailed description-set forth below, and in part will be apparent from the description, or may be learned by practice of the subject technology. It is to be understood that both the foregoing general description and the following detailed description are exemplary and explanatory and are intended to provide further explanation of the present invention as claimed.

BRIEF DESCRIPTION OF THE FIGURES

The accompanying drawings, which are included to provide further understanding of the present invention and are incorporated in and constitute a part of this specification, illustrate aspects of the subject technology and together with the description serve to explain the principles of the present invention.

DETAILED DESCRIPTION OF THE INVENTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

In the following detailed description, numerous specific details are set forth to provide a full understanding of the present invention. It will be apparent, however, to one of ordinarily skilled in the art that the subject technology may be practiced without some of these specific details. In other instances, well-known structures and techniques have not been shown in detail so as not to obscure the present invention.

Unless defined otherwise, all technical and scientific terms used herein have the same meaning as commonly understood by one of ordinary skill in the art to which this invention belongs.

Without wishing to be bound by this theory, the inventors believe that although the neutrophilic dermatoses (NDs) are a heterogeneous group of conditions, they have common features and overlapping pathophysiology which involves the IL-36 pathway. While a neutrophilic dermatosis is associated primarily with cutaneous manifestations due to accumulation of neutrophils, IL-36 plays an important role in driving disease manifestation, particularly, in pustular NDs such as subcorneal pustulosis (Sneddon-Wilkinson), pustular psoriasis, acute generalized exanthematic pustulosis (AGEP), infantile acropustulosis (IA), Behcet disease, pustulosis, hyperostosis and osteitis (SAPHO) syndrome, Bowel-associated dermatosis-arthritis syndrome (BADAS), Neutrophilic dermatosis of the dorsal hands (NDDH), Amicrobial pustulosis of the skinfolds (APF). Additionally, blocking IL-36 pathway may be beneficial in skin inflammation with papules, nodules and plaques such as acute febrile neutrophilic dermatoses (Sweet's syndrome), rheumatoid neutrophilic dermatitis (RND), neutrophilic eccrine hidradenitis (NEH), erythema elevatum diutinum (EED) and or with skin ulcerations such as pyoderma gangrenosum (PG). The IL-36 blockade is also beneficial in patients with ichthyosis (and its subtypes including netherton syndrome or NS).

In one aspect, the present invention relates to a method for treating, preventing or ameliorating a neutrophilic dermatosis (ND) in a subject, comprising administering to the subject a therapeutically effective amount of an anti-IL-36R antibody or an antigen-binding fragment thereof (as disclosed herein). In an embodiment relating to this aspect, the anti-IL-36R antibody is spesolimab.

Figure 1:
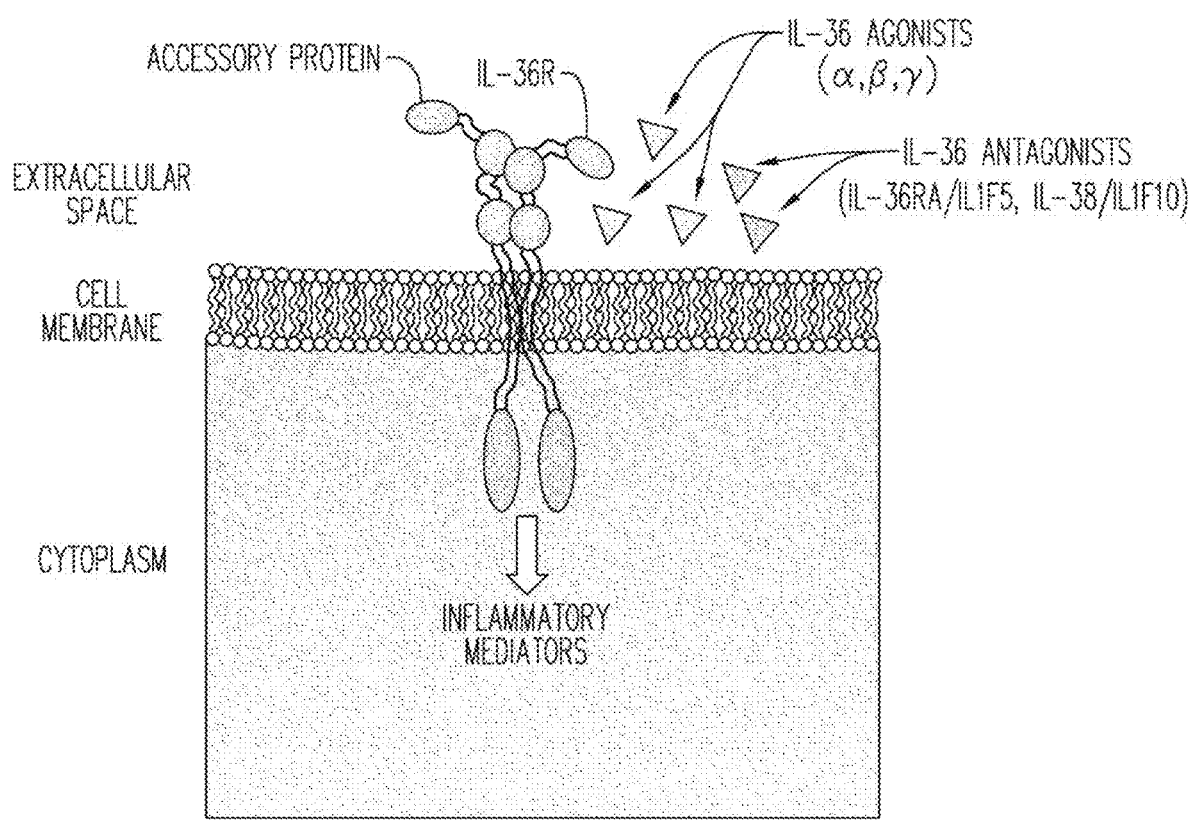
FIG. 1 shows the IL-36 antagonist ligands (IL-36RA/IL1F5, IL-38/ILF10) inhibiting the signaling cascade.
Figure 2:
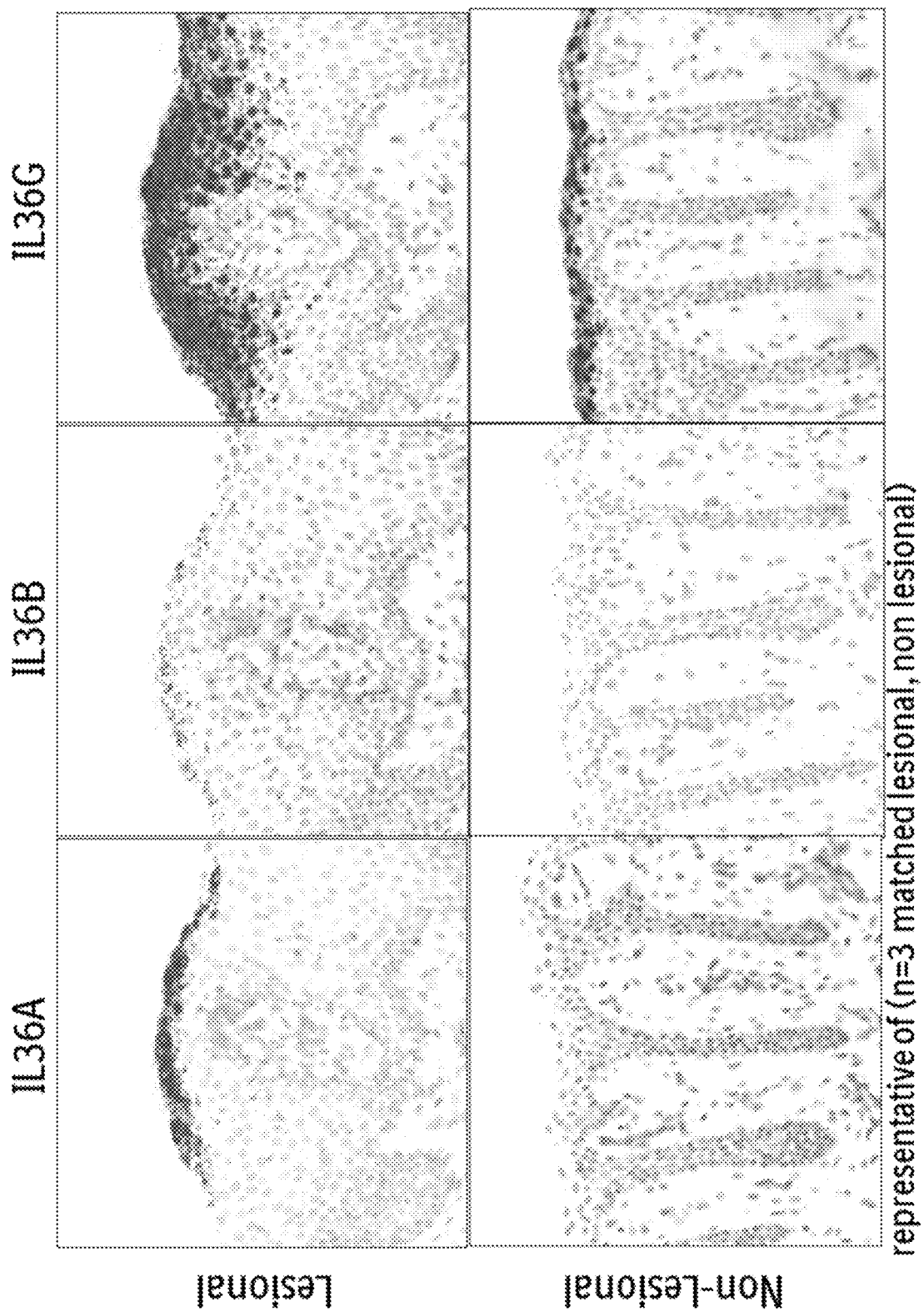
FIG. 2 shows IL-36 Ligand expression by in situ hybridization (ISH) techniques in human skin biopsies. It shows formalin fixed paraffin embedded (FFPE) skin biopsies from HS lesional and non-lesional HS samples were purchased from a vendor and using ISH probes, stained for IL-36 α, β, γ. Increased expression of as all three IL36 ligands, α, β γ are seen in HS skin samples.

Without wishing to be bound by this theory it is believed that anti-IL-36R antibodies or antigen-binding fragments thereof bind to human IL-36R and thus interfere with the binding of IL-36 agonists, and in doing so block at least partially the signaling cascade from the IL-36R to inflammatory mediators involved in neutrophilic dermatoses. This is illustrated by FIG. 1. IL-36R is also known as IL-1RL2 and IL-1Rrp2. It has been reported that agonistic IL-36 ligands (α, β, or γ) initiate the signaling cascade by engaging the IL-36 receptor which then forms a heterodimer with the IL-1 receptor accessory protein (IL-1RAcP).

The anti-IL36R antibodies of the present invention are disclosed herein an in, for example, in U.S. Pat. No. 9,023,995, the entire content of which is incorporated herein by reference.

Definitions

A phrase such as "an aspect" does not imply that such aspect is essential to the present invention or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure.

The term "about" shall generally mean an acceptable degree of error or variation for the quantity measured given the nature or precision of the measurements. Typical, exemplary degrees of error or variation are within 5% or within 3% or within 1% of a given value or range of values. For example, the expression of "about 100" includes 105 and 95 or 103 and 97 or 101 and 99, and all values in between (e.g., 95.1, 95.2, etc. for range of 95-105; or 97.1, 97.2, etc. for the range of 97-103; 99.1, 99.2, etc. for the range of 99-101). Numerical quantities given herein are approximates unless stated otherwise, meaning that the term "about" can be inferred when not expressly stated.

A "pharmaceutical composition" refers in this context to a liquid or powder preparation which is in such form as to permit the biological activity of the active ingredient(s) to be unequivocally effective, and which contains no additional components which are significantly toxic to the subjects to which the composition would be administered. Such compositions are sterile.

The term "subject" for purposes of treatment refers to any animal classified as a mammal, including humans, domesticated and farm animals, and zoo, sports, or pet animals, such as dogs, horses, cats, cows, and the like. Preferably, the mammal is human.

As used herein, the terms "treat", "treating", or the like, mean to alleviate symptoms, eliminate the causation of symptoms either on a temporary or permanent basis, or to prevent or slow the appearance of symptoms of the named disorder or condition. These terms are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder thereby preventing or removing one or more signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the humanized anti-IL-36R antibody composition, the result should be considered an effective treatment of the underlying disorder regardless of whether all the symptoms of the disorder are alleviated or not.

The term "therapeutically effective amount" is used to refer to an amount of an active agent that relieves or ameliorates one or more of the symptoms of the disorder being treated. In another aspect, the therapeutically effective amount refers to a target serum concentration that has been shown to be effective in, for example, slowing disease progression.

Although any methods and materials similar or equivalent to those described herein can be used in the practice of the present invention, the preferred methods and materials are now described. All publications mentioned herein are incorporated herein by reference to describe in their entirety.

As mentioned earlier, the neutrophilic dermatoses (NDs) are a heterogeneous group of conditions that have common features and overlapping pathophysiology. Neutrophilic dermatoses include hidradenitis suppurativa (HS); acute generalized exanthematous pustulosis; acute febrile neutrophilic dermatosis (Sweet syndrome); amicrobial pustulosis of the folds (APF); Behcet disease; Bowel bypass syndrome (bowel-associated dermatitis-arthritis syndrome); bowel-associated dermatosis-arthritis syndrome (BADAS); CARD14-mediated pustular psoriasis (CAMPS); cryopyrin associated periodic syndromes (CAPS); deficiency of interleukin-36 receptor antagonist (DITRA); deficiency of interleukin-I receptor antagonist (DIRA); erythema elevatum diutinum; Histiocytoid neutrophilic dermatitis; infantile acropustulosis; neutrophilic dermatosis of the dorsal hands; neutrophilic eccrine hidradenitis; neutrophilic urticarial dermatosis; palisading neutrophilic granulomatous dermatitis; plaque psoriasis; pyoderma gangrenosum, acne, and hidradenitis suppurativa (PASH) syndrome; pyoderma gangrenosum (PG); pyoderma gangrenosum and acne (PAPA); pyogenic arthritis; skin lesions of Behcet's disease; Still's disease; subcorneal pustulosis (Sneddon-Wilkinson); synovitis, acne, pustulosis-hyperostosis; ostcitis (SAPHO) syndrome; rheumatoid neutrophilic dermatitis (RND), and ichthyosis (and its subtypes including netherton syndrome or NS).

For example, hidradenitis suppurativa (HS) is an inflammatory disease characterized by recurrent, painful abscesses and fistulous tracts. Patients with HS objectively have one of the lowest quality of life measures of any dermatologic disease. Lesions characteristically occur in the axillary, groin, infra-mammary, and/or anogenital regions of the body. HS lesions may progress to form sinus tracts and expansive abscesses. Sequelae include significant pain, scarring, and psychological distress. The contribution of various inflammatory pathways in driving the disease pathogenesis is emerging. It has been shown that IL36 ligands are upregulated in the lesional skin of HS patients and in circulation (Di Caprio et al., 2017; Hessam et al., 2018 (Thomi et al., 2017).

IL36R is a novel member of the IL1R family that forms a heterodimeric complex with the IL1R accessory protein (IL1RAcp) and IL1Rrp2 associated with epithelial mediated inflammation and barrier dysfunction. The heterodimeric IL36R system with stimulating (IL36α, IL36β, IL36γ) and inhibitory ligands (IL36Ra and IL38) shares a number of structural and functional similarities to other members of the IL1/ILR family, such as IL1, IL18 and IL33. All IL1 family members (IL1α, IL1β, IL18, IL36α, IL36β, IL36γ, and IL38) signal through a unique, cognate receptor protein which, upon ligand binding, recruits the common IL1RAcP subunit and activates NFγB and MAP kinase pathways in receptor-positive cell types (Dinarello, 2011; Towne et al., 2004; Towne et al., 2011). Genetic human studies have established a strong link between IL36R signaling and skin inflammation as demonstrated by occurrence of generalized pustular psoriasis in patients with a loss of function mutation in IL36Ra which results in uncontrolled IL36R signaling (Marrakchi et al., 2011).

While there is no animal model data for HS, expression and function of this pathway in various disease relevant cell types link it to skin inflammation. IL36R is expressed in epithelial cells (e.g. keratinocytes, intestinal epithelial cells), dermal fibroblasts, and immune cells (myeloid cells, B cells and T cells). Mice deficient of IL36R receptor had significantly reduced skin inflammation and keratinocyte proliferation compared to wild-type controls.

Given the strong connection between the IL36 pathway and neutrophilic dermatoses, without wishing to be bound by this theory, it is believed that IL36R biology contributes to pathophysiology of these conditions and hence blocking IL36R activation will be beneficial in patients suffering from a neutrophilic dermatosis.

Therefore, the present invention includes methods for treating a subject in need thereof, said method comprising administering a therapeutically effective amount of an anti-IL-36R antibody or an antigen binding fragment thereof to the subject. As used herein, the expression "a subject in need thereof" means a human or a non-human animal that exhibits one or more symptoms of a neutrophilic dermatosis, e.g., neutrophilic infiltration in affected skin tissues, pustules, etc., and/or who has been diagnosed with a neutrophilic dermatosis condition.

In an embodiment, a subject suffering from a neutrophilic dermatosis may also have a skin infection selected from the group consisting of impetigo, cellulitis, infected dermatitis, eczema herpeticum, folliculitis, infected blister, mycosis, tinea *versicolor, Staphylococcus aureus* infection, and *Streptococcus* infection. A microbe that cause the infection includes, but is not limited to *Staphylococcus aureus, Streptococcus* spp., *Pseudomonas aeruginosa, Bacteroides* spp., Herpes simplex virus, coxsackievirus, molluscum contagiosum virus, vaccinia virus, *Candida albicans, Microsporum* spp., *Trichophyton* spp., *Penicillium* spp., *Cladosporium* spp., *Alternaria* spp., and *Aspergillus* spp.

The present invention provides methods to reduce microbial colonization of the skin in a subject with a neutrophilic dermatosis comprising administering a therapeutically effective amount of an anti-IL-36R antibody or an antigen binding fragment thereof to the subject. In certain embodiments, the invention provides for methods to reduce colonization of *S. aureus* on the skin of patients with a neutrophilic dermatosis. In some embodiments, the microbial colonization is reduced by at least 10%, at least 15%, at least 20%, at least 25%, at least 30%, at least 35%, at least 40%, at least 45%, at least 50%, at least 55%, at least 60%, at least 65%, at least 70%, or at least 75% as compared to the baseline, upon administration of the anti-IL-36R antibody.

Microbial colonization may be measured with tests and procedures known in the art, e.g., by PCR, microbial culture, microscopy and staining or immunofluorescence. In certain embodiments, microbial colonization may be measured by the presence of microbial protein biomarkers known in the art, e.g., microbial toxin such as staph toxic shock syndrome toxin-1. Methods for detecting and/or quantifying such biomarkers are known in the art.

Antibodies of the Present Invention

The anti-IL36R antibodies of the present invention are disclosed in U.S. Pat. No. 9,023,995 or WO2013/074569, the entire content of each of which is incorporated herein by reference.

The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-36R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F (ab') 2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind IL-36R. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-36R, as used in the context of the present invention, includes antibodies that bind IL-36R or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-36R may, however, have cross-reactivity to other antigens, such as IL-36R molecules from other (non-human) species.

In certain exemplary embodiments related to any aspects of the present invention, the anti-IL-36R antibody or antigen-binding fragment thereof that can be used in the context of the methods of the present invention includes: a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 53 or 141 (H-CDR1); the amino acid sequence of SEQ ID NO: 62, 108, 109, 110, 111 or 142 (H-CDR2); the amino acid sequence of SEQ ID NO: 72 (H-CDR3).

According to certain embodiments, the anti-IL-36R antibody or antigen-binding fragment thereof comprises:

I. a) a light chain variable region comprising the amino acid sequence of SEQ ID NO: 26 (L-CDR1); the amino acid sequence of SEQ ID NO: 102 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or II. a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or III. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or IV. a) a light chain variable region comprising the amino acid sequence of SEQ ID NO: 26 (L-CDR1); the amino acid sequence of SEQ ID NO: 105 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or V. a) a light chain variable region comprising the amino acid sequence of SEQ ID NO: 26 (L-CDR1); the amino acid sequence of SEQ ID NO: 106 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3) or VI. a) a light chain variable region comprising the amino acid sequence of SEQ ID NO: 26 (L-CDR1); the amino acid sequence of SEQ ID NO: 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VII. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 141 (H-CDR1); the amino acid sequence of SEQ ID NO: 62, 108, 109, 110, 111 or 142 (H-CDR2); the amino acid sequence of SEQ ID NO: 72 (H-CDR3).

According to certain embodiments, the anti-IL-36R antibody or antigen-binding fragment thereof comprises:

(i) a light chain variable region comprising the amino acid sequence of SEQ ID NO: 77; and a heavy chain variable region comprising the amino acid sequence of SEQ ID NO: 87; or (ii) a light chain variable region comprising the amino acid sequence of SEQ ID NO: 77; and a heavy chain variable region comprising the amino acid sequence of SEQ ID NO: 88; or (iii) a light chain variable region comprising the amino acid sequence of SEQ ID NO: 77; and a heavy chain variable region comprising the amino acid sequence of SEQ ID NO: 89; or (iv) a light chain variable region comprising the amino acid sequence of SEQ ID NO: 80; and a heavy chain variable region comprising the amino acid sequence of SEQ ID NO: 87; or (v) a light chain variable region comprising the amino acid sequence of SEQ ID NO: 80; and a heavy chain variable region comprising the amino acid sequence of SEQ ID NO: 88; or (vi) a light chain variable region comprising the amino acid sequence of SEQ ID NO: 80; and a heavy chain variable region comprising the amino acid sequence of SEQ ID NO: 89; or (vii) a light chain variable region comprising the amino acid sequence of SEQ ID NO: 85; and a heavy chain variable region comprising the amino acid sequence of SEQ ID NO: 100; or (viii) a light chain variable region comprising the amino acid sequence of SEQ ID NO: 85; and a heavy chain variable region comprising the amino acid sequence of SEQ ID NO:101; or (ix) a light chain variable region comprising the amino acid sequence of SEQ ID NO: 86; and a heavy chain variable region comprising the amino acid sequence of SEQ ID NO: 100; or (x) a light chain variable region comprising the amino acid sequence of SEQ ID NO: 86; and a heavy chain variable region comprising the amino acid sequence of SEQ ID NO:101.

According to certain embodiments, the anti-IL-36R antibody or antigen-binding fragment thereof comprises:

i. a light chain comprising the amino acid sequence of SEQ ID NO: 115; and a heavy chain comprising the amino acid sequence of SEQ ID NO: 125; or ii. a light chain comprising the amino acid sequence of SEQ ID NO: 115; and a heavy chain comprising the amino acid sequence of SEQ ID NO: 126; or iii. a light chain comprising the amino acid sequence of SEQ ID NO: 115; and a heavy chain comprising the amino acid sequence of SEQ ID NO: 127; or iv. a light chain comprising the amino acid sequence of SEQ ID NO: 118; and a heavy chain comprising the amino acid sequence of SEQ ID NO: 125; or v. a light chain comprising the amino acid sequence of SEQ ID NO: 118; and a heavy chain comprising the amino acid sequence of SEQ ID NO: 126; or vi. a light chain comprising the amino acid sequence of SEQ ID NO: 118; and a heavy chain comprising the amino acid sequence of SEQ ID NO: 127; or vii. a light chain comprising the amino acid sequence of SEQ ID NO: 123; and a heavy chain comprising the amino acid sequence of SEQ ID NO: 138; or viii. a light chain comprising the amino acid sequence of SEQ ID NO: 123; and a heavy chain comprising the amino acid sequence of SEQ ID NO: 139; or ix. a light chain comprising the amino acid sequence of SEQ ID NO: 124; and a heavy chain comprising the amino acid sequence of SEQ ID NO: 138.

In one aspect, described and disclosed herein are anti-IL-36R antibodies, in particular humanized anti-IL-36R antibodies, and compositions and articles of manufacture comprising one or more anti-IL-36R antibody, in particular one or more humanized anti-IL-36R antibody of the present invention. Also described are binding agents that include an antigen-binding fragment of an anti-IL-36 antibody, in particular a humanized anti-IL-36R antibody.

Therapeutic Uses of the Antibodies

Increasingly, the role of neutrophils in skin inflammation is being understood. While the role of IL-36 pathway in generalized pustular psoriasis based on genetics and proven inhibition with spesolimab is clear, the involvement of the same pathway in other similar neutrophilic dermatoses (NDs), which are a heterogeneous set of conditions with common features and overlapping pathophysiology, is being appreciated. While the disease is associated primarily with cutaneous manifestations due to accumulation of neutrophils, the involvement of additional tissues is also seen. Our studies suggest that the IL-36 pathway plays an important role in driving disease manifestations in pustular NDs such as subcorneal pustulosis (Sneddon-Wilkinson), Pustular psoriasis, Palmoplantar pustulosis, Acute generalized exanthematic pustulosis (AGEP), Infantile acropustulosis (IA), Behcet disease, pustulosis, hyperostosis and osteitis (SAPHO) syndrome, Bowel-associated dermatosis-arthritis syndrome (BADAS), Neutrophilic dermatosis of the dorsal hands (NDDH), Amicrobial pustulosis of the skinfolds (APF). Accordingly, blocking the IL-36 pathway should be beneficial in skin inflammation with papules, nodules and plaques such as acute febrile neutrophilic dermatoses (Sweet's syndrome), rheumatoid neutrophilic dermatitis (RND), neutrophilic eccrine hidradenitis (NEH), erythema elevatum diutinum (EED) and or with skin ulcerations such as pyoderma gangrenosum (PG). The IL-36 blockade should also be beneficial in patients with ichthyosis (and its subtypes including Netherton syndrome or NS)

The present invention provides anti-IL-36R antibodies and a pharmaceutical composition comprising an anti-IL-36R antibody for use in reducing, diminishing or blocking the IL-36 pathway which is useful for the treatment or prevention of neutrophilic dermatoses in subjects, preferably humans.

In one aspect, the present invention relates to a method for treating, preventing or ameliorating a neutrophilic dermatosis (ND) in a subject, comprising administering to the subject a therapeutically effective amount of an anti-IL-36R antibody or an antigen-binding fragment thereof (as disclosed herein). In an embodiment relating to this aspect, the anti-IL-36R antibody is spesolimab.

In one aspect, the present invention relates to a method of treating a skin disorder associated with neutrophilic dermatoses in a patient, said method(s) including administering or having administered to the patient a therapeutically effective amount of an anti-IL-36R antibody of the present invention or an antigen binding fragment thereof (as disclosed herein). In an embodiment relating to this aspect, the anti-IL-36R antibody is spesolimab.

In one aspect, the present invention relates to a method of treating skin inflammation associated with neutrophilic dermatoses in a subject, said method including administering or having administered to the subject a therapeutically effective amount of an anti-IL-36R antibody of the present invention or an antigen binding fragment thereof (as disclosed herein). In an embodiment relating to this aspect, the anti-IL-36R antibody is spesolimab.

In one aspect, the present invention relates to a method preventing or reducing neutrophilic infiltrates in affected skin tissues in a subject suffering from a neutrophilic dermatosis, said method including administering or having administered to the subject a therapeutically effective amount of an anti-IL-36R antibody of the present invention or an antigen binding fragment thereof. In an embodiment relating to this aspect, the anti-IL-36R antibody is spesolimab.

In one aspect, the present invention relates to a method of reducing microbial colonization of the skin in a subject with neutrophilic dermatosis comprising administering to the subject a therapeutically effective amount of an anti-IL-36R antibody or an antigen-binding fragment thereof, as disclosed herein. In an embodiment relating to this aspect, the colonization is of a microbe selected from the group consisting of *Staphylococcus aureus, Streptococcus* spp., *Pseudomonas aeruginosa, Bacteroides* spp., molluscum contagiosum virus, Herpes simplex virus, coxsackievirus, vaccinia virus, *Candida albicans, Microsporum* spp., *Trichophyton* spp., *Penicillium* spp., *Cladosporium* spp., *Alternaria* spp., and *Aspergillus* spp. In another embodiment relating to this aspect, the microbe is *Staphylococcus aureus* (*S. aureus*). In another embodiment relating to this aspect, the *S. aureus* colonization is reduced by at least 10% or by at least 20% from the baseline following the administration of the anti-IL-36R antibody or an antigen-binding fragment thereof, as disclosed herein. In an embodiment relating to this aspect, the anti-IL-36R antibody is spesolimab.

In one aspect, the present invention relates to a method of reducing susceptibility to a skin infection in a subject with neutrophilic dermatosis comprising administering to the subject a therapeutically effective amount of an anti-IL-36-R antibody or an antigen-binding fragment thereof (as disclosed herein). In an embodiment relating to this aspect, the skin infection is caused by a microbe selected from the group consisting of *Staphylococcus aureus, Streptococcus* spp., *Pseudomonas aeruginosa, Bacteroides* spp., Herpes simplex virus, molluscum contagiosum virus, coxsackievirus, vaccinia virus, *Candida albicans, Microsporum* spp., *Trichophyton* spp., *Penicillium* spp., *Cladosporium* spp., *Alternaria* spp., and *Aspergillus* spp. In another embodiment relating to this aspect, the microbe is *Staphylococcus aureus* (*S. aureus*). In an embodiment relating to this aspect, the anti-IL-36R antibody is spesolimab.

In an embodiment relating to any of the above aspects, a second therapeutic agent is administered to the subject before, after, or concurrent with the anti-IL-36R antibody or an antigen-binding fragment thereof. In a related embodiment, the second therapeutic agent is selected from the group consisting of an anti-bacterial agent, an anti-viral agent, an anti-fungal agent, another IL-36R antagonist, an IgE inhibitor, a corticosteroid, NSAID, an IL-4R antagonist, and IFNγ.

In an embodiment relating to any of the above aspects, the anti-IL-36R antibody includes: a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 53 or 141 (H-CDR1); the amino acid sequence of SEQ ID NO: 62, 108, 109, 110, 111 or 142 (H-CDR2); the amino acid sequence of SEQ ID NO: 72 (H-CDR3).

In an embodiment relating to any of the above aspects, the anti-IL-36R antibody includes: a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 141 (H-CDR1); the amino acid sequence of SEQ ID NO: 62, 108, 109, 110, 111 or 142 (H-CDR2); the amino acid sequence of SEQ ID NO: 72 (H-CDR3).

In an embodiment relating to any of the above aspects, the anti-IL-36R antibody includes:

I. a) a light chain variable region comprising the amino acid sequence of SEQ ID NO: 26 (L-CDR1); the amino acid sequence of SEQ ID NO: 102 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or II. a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or III. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or IV. a) a light chain variable region comprising the amino acid sequence of SEQ ID NO: 26 (L-CDR1); the amino acid sequence of SEQ ID NO: 105 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or V. a) a light chain variable region comprising the amino acid sequence of SEQ ID NO: 26 (L-CDR1); the amino acid sequence of SEQ ID NO: 106 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VI. a) a light chain variable region comprising the amino acid sequence of SEQ ID NO: 26 (L-CDR1); the amino acid sequence of SEQ ID NO: 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VII. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 141 (H-CDR1); the amino acid sequence of SEQ ID NO: 62, 108, 109, 110, 111 or 142 (H-CDR2); the amino acid sequence of SEQ ID NO: 72 (H-CDR3).

In an embodiment relating to any of the above aspects, the anti-IL-36R antibody includes:

(i) a light chain variable region comprising the amino acid sequence of SEQ ID NO: 77; and a heavy chain variable region comprising the amino acid sequence of SEQ ID NO: 87; or (ii) a light chain variable region comprising the amino acid sequence of SEQ ID NO: 77; and a heavy chain variable region comprising the amino acid sequence of SEQ ID NO: 88; or (iii) a light chain variable region comprising the amino acid sequence of SEQ ID NO: 77; and a heavy chain variable region comprising the amino acid sequence of SEQ ID NO: 89; or (iv) a light chain variable region comprising the amino acid sequence of SEQ ID NO: 80; and a heavy chain variable region comprising the amino acid sequence of SEQ ID NO: 87; or (v) a light chain variable region comprising the amino acid sequence of SEQ ID NO: 80; and a heavy chain variable region comprising the amino acid sequence of SEQ ID NO: 88; or (vi) a light chain variable region comprising the amino acid sequence of SEQ ID NO: 80; and a heavy chain variable region comprising the amino acid sequence of SEQ ID NO: 89; or (vii) a light chain variable region comprising the amino acid sequence of SEQ ID NO: 85; and a heavy chain variable region comprising the amino acid sequence of SEQ ID NO: 100; or
(viii) a light chain variable region comprising the amino acid sequence of SEQ ID NO: 85; and a heavy chain variable region comprising the amino acid sequence of SEQ ID NO:101; or
(ix) a light chain variable region comprising the amino acid sequence of SEQ ID NO: 86; and a heavy chain variable region comprising the amino acid sequence of SEQ ID NO: 100; or
(x) a light chain variable region comprising the amino acid sequence of SEQ ID NO: 86; and a heavy chain variable region comprising the amino acid sequence of SEQ ID NO:101.

In an embodiment relating to any of the above aspects, the anti-IL-36R antibody includes:
i. a light chain comprising the amino acid sequence of SEQ ID NO: 115; and a heavy chain comprising the amino acid sequence of SEQ ID NO: 125; or
ii. a light chain comprising the amino acid sequence of SEQ ID NO: 115; and a heavy chain comprising the amino acid sequence of SEQ ID NO: 126; or
iii. a light chain comprising the amino acid sequence of SEQ ID NO: 115; and a heavy chain comprising the amino acid sequence of SEQ ID NO: 127; or
iv. a light chain comprising the amino acid sequence of SEQ ID NO: 118; and a heavy chain comprising the amino acid sequence of SEQ ID NO: 125; or
v. a light chain comprising the amino acid sequence of SEQ ID NO: 118; and a heavy chain comprising the amino acid sequence of SEQ ID NO: 126; or
vi. a light chain comprising the amino acid sequence of SEQ ID NO: 118; and a heavy chain comprising the amino acid sequence of SEQ ID NO: 127; or
vii. a light chain comprising the amino acid sequence of SEQ ID NO: 123; and a heavy chain comprising the amino acid sequence of SEQ ID NO: 138; or
viii. a light chain comprising the amino acid sequence of SEQ ID NO: 123; and a heavy chain comprising the amino acid sequence of SEQ ID NO: 139; or
ix. a light chain comprising the amino acid sequence of SEQ ID NO: 124; and a heavy chain comprising the amino acid sequence of SEQ ID NO: 138.

In an embodiment relating to any of the above aspects and embodiments, the neutrophilic dermatosis is selected from the group consisting of hidradenitis suppurativa (HS); acute generalized exanthematous pustulosis; acute febrile neutrophilic dermatosis (Sweet syndrome); amicrobial pustulosis of the folds (APF); Behcet disease; Bowel bypass syndrome (bowel-associated dermatitis-arthritis syndrome); bowel-associated dermatosis-arthritis syndrome (BADAS); CARD14-mediated pustular psoriasis (CAMPS); cryopyrin associated periodic syndromes (CAPS); deficiency of interleukin-36 receptor antagonist (DITRA); deficiency of interleukin-I receptor antagonist (DIRA); erythema elevatum diutinum; Histiocytoid neutrophilic dermatitis; infantile acropustulosis; neutrophilic dermatosis of the dorsal hands; neutrophilic eccrine hidradenitis; neutrophilic urticarial dermatosis; palisading neutrophilic granulomatous dermatitis; plaque psoriasis; pyoderma gangrenosum, acne, and hidradenitis suppurativa (PASH) syndrome; pyoderma gangrenosum (PG); pyoderma gangrenosum and acne (PAPA); pyogenic arthritis; skin lesions of Behcet's disease; Still's disease; subcorneal pustulosis (Sneddon-Wilkinson); synovitis, acne, pustulosis-hyperostosis; ostcitis (SAPHO) syndrome; rheumatoid neutrophilic dermatitis (RND), and ichthyosis (and its subtypes including Netherton syndrome or NS).

In a related embodiment, the neutrophilic dermatosis is hidradenitis suppurativa (HS). In a related embodiment, the neutrophilic dermatosis is acute generalized exanthematous pustulosis. In a related embodiment, the neutrophilic dermatosis is acute febrile neutrophilic dermatosis (Sweet syndrome). In a related embodiment, the neutrophilic dermatosis is amicrobial pustulosis of the folds (APF). In a related embodiment, the neutrophilic dermatosis is Behcet disease. In a related embodiment, the neutrophilic dermatosis is bowel bypass syndrome (bowel-associated dermatitis-arthritis syndrome). In a related embodiment, the neutrophilic dermatosis is bowel-associated dermatosis-arthritis syndrome (BADAS). In a related embodiment, the neutrophilic dermatosis is CARD14-mediated pustular psoriasis (CAMPS). In a related embodiment, the neutrophilic dermatosis is cryopyrin associated periodic syndromes (CAPS). In a related embodiment, the neutrophilic dermatosis is deficiency of interleukin-36 receptor antagonist (DITRA). In a related embodiment, the neutrophilic dermatosis is deficiency of interleukin-I receptor antagonist (DIRA). In a related embodiment, the neutrophilic dermatosis is erythema elevatum diutinum. In a related embodiment, the neutrophilic dermatosis is Histiocytoid neutrophilic dermatitis. In a related embodiment, the neutrophilic dermatosis is infantile acropustulosis. In a related embodiment, the neutrophilic dermatosis is neutrophilic dermatosis of the dorsal hands. In a related embodiment, the neutrophilic dermatosis is neutrophilic eccrine hidradenitis. In a related embodiment, the neutrophilic dermatosis is neutrophilic urticarial dermatosis. In a related embodiment, the neutrophilic dermatosis is palisading neutrophilic granulomatous dermatitis. In a related embodiment, the neutrophilic dermatosis is plaque psoriasis. In a related embodiment, the neutrophilic dermatosis is pyoderma gangrenosum, acne, and hidradenitis suppurativa (PASH) syndrome. In a related embodiment, the neutrophilic dermatosis is pyoderma gangrenosum (PG). In a related embodiment, the neutrophilic dermatosis is pyoderma gangrenosum and acne (PAPA). In a related embodiment, the neutrophilic dermatosis is pyogenic arthritis. In a related embodiment, the neutrophilic dermatosis is skin lesions of Behcet's disease. In a related embodiment, the neutrophilic dermatosis is Still's disease. In a related embodiment, the neutrophilic dermatosis is subcorneal pustulosis (Sneddon-Wilkinson). In a related embodiment, the neutrophilic dermatosis is synovitis, acne, pustulosis-hyperostosis and ostcitis (SAPHO) syndrome. In a related embodiment, the neutrophilic dermatosis is rheumatoid neutrophilic dermatitis (RND). In a related embodiment, the neutrophilic dermatosis is ichthyosis (and its subtypes including Netherton syndrome or NS).

In another embodiment relating to any of the above aspects or embodiments described herein, the anti-IL-36R antibody is administered in the range of 0.001 to 1000 mg to a subject suffering from a neutrophilic dermatosis.

In another embodiment relating to any of the above aspects or embodiments described herein, the anti-IL-36R antibody is spesolimab.

In another embodiment relating to any of the above aspects or embodiments described herein, the therapeutic effective amount of the anti-interleukin-36 receptor (anti-IL-36R) antibody is in the range of about 0.001 to about 1000 mg.

In another embodiment relating to any of the above aspects or embodiments described herein, a second therapeutic agent is administered to the subject before, after, or concurrent with the anti-IL-36R antibody.

In another embodiment relating to any of the above aspects or embodiments described herein, the second therapeutic agent is selected from the group consisting of an anti-bacterial agent, an anti-viral agent, an anti-fungal agent, an anti-IL-36R antibody, an IgE inhibitor, a corticosteroid, a non-steroid anti-inflammatory drug (NSAID), an IL-4R antagonist, and IFN-γ.

Pharmaceutical Composition

An antibody of the invention can be incorporated into pharmaceutical compositions suitable for administration to a subject. The compounds of the invention may be administered alone or in combination with a pharmaceutically acceptable carrier, diluent, and/or excipients, in single or multiple doses. The pharmaceutical compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions are designed in accordance with conventional techniques as in e.g., Remington, The Sience and Practice of Phannacy, 19th Edition, Gennaro, Ed., Mack Publishing Co., Easton, P A 1995 which provides a compendium of formulation techniques as are generally known to practitioners.

A pharmaceutical composition comprising an anti-IL-36R monoclonal antibody of the present invention can be administered to a subject suffering from a neutrophilic dermatosis as described herein using standard administration techniques including oral, intravenous, intraperitoneal, subcutaneous, pulmonary, transdermal, intramuscular, intranasal, buccal, sublingual, or suppository administration.

The route of administration of an antibody of the present invention may be oral, parenteral, by inhalation, or topical. Preferably, the antibodies of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred. Suitable vehicles for such injections are known in the art.

The pharmaceutical composition typically must be sterile and stable under the conditions of manufacture arid storage in the container provided, including e.g., a sealed vial or syringe. Therefore, pharmaceutical compositions may be sterile filtered after making the formulation, or otherwise made microbiologically acceptable. A typical composition for intravenous infusion could have a volume as much as 250-1000 ml of fluid, such as sterile Ringer's solution, physiological saline, dextrose solution and Hank's solution and a therapeutically effective dose, (e.g., 1 to 100 mg/mL or more) of antibody concentration. Dose may vary depending on the type and severity of the disease. As is well known in the medical arts, dosages for any one subject depends upon many factors, including the patient's size, body surface area, age, the particular compound to be administered, sex, time and route of administration, general health, and other drugs being administered concurrently. A typical dose can be, for example, in the range of 0.001 to 1000 mg; however, doses below or above this exemplary range are envisioned, especially considering the aforementioned factors.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the humanized anti-IL-36R antibody. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

The following examples are intended to further illustrate certain preferred embodiments of the disclosure and are not limiting in nature. Those skilled in the art will recognize or be able to ascertain numerous equivalents to the specific substances and procedures described herein.

Example 1: Treating Patients with Neutrophilic Dermatoses

In this example, an anti-IL36R antibody of the present invention is used to treat patients with neutrophilic dermatoses.

Following the administration of the anti-IL-36R antibody, safety and efficacy assessments reveal the following: At least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% of the patients show improvements over baseline or as compared to placebo.

Example 2: Treating Patients with a Hidradenitis Suppurativa (HS)

In this example, an anti-IL36R antibody of the present invention is used to treat patients with HS.

Following the administration of the anti-IL-36R antibody, safety and efficacy assessments reveal the following: At least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% of the patients show improvements over baseline or as compared to placebo.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

All patents and/or publications including journal articles cited in this disclosure are expressly incorporated herein by reference.

The invention claimed is:

1. A method for treating pyoderma gangrenosum (PG) in a subject comprising administering to the subject a therapeutically effective amount of an anti-interleukin-36 receptor (anti-IL-36R) antibody.

2. The method of claim 1, wherein the anti-IL-36R antibody comprises:

I. a) a light chain variable region comprising the amino acid sequence of SEQ ID NO: 26 (L-CDR1); the amino acid sequence of SEQ ID NO: 102 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or II. a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or III. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or IV. a) a light chain variable region comprising the amino acid sequence of SEQ ID NO: 26 (L-CDR1); the amino acid sequence of SEQ ID NO: 105 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or V. a) a light chain variable region comprising the amino acid sequence of SEQ ID NO: 26 (L-CDR1); the amino acid sequence of SEQ ID NO: 106 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VI. a) a light chain variable region comprising the amino acid sequence of SEQ ID NO: 26 (L-CDR1); the amino acid sequence of SEQ ID NO: 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VII. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 141 (H-CDR1); the amino acid sequence of SEQ ID NO: 62, 108, 109, 110, 111 or 142 (H-CDR2); the amino acid sequence of SEQ ID NO: 72 (H-CDR3).

3. The method claim 1, wherein the anti-IL-36R antibody comprises:
(i) a light chain variable region comprising the amino acid sequence of SEQ ID NO: 77; and a heavy chain variable region comprising the amino acid sequence of SEQ ID NO: 87; or
(ii) a light chain variable region comprising the amino acid sequence of SEQ ID NO: 77; and a heavy chain variable region comprising the amino acid sequence of SEQ ID NO: 88; or
(iii) a light chain variable region comprising the amino acid sequence of SEQ ID NO: 77; and a heavy chain variable region comprising the amino acid sequence of SEQ ID NO: 89; or
(iv) a light chain variable region comprising the amino acid sequence of SEQ ID NO: 80; and a heavy chain variable region comprising the amino acid sequence of SEQ ID NO: 87; or
(v) a light chain variable region comprising the amino acid sequence of SEQ ID NO: 80; and a heavy chain variable region comprising the amino acid sequence of SEQ ID NO: 88; or
(vi) a light chain variable region comprising the amino acid sequence of SEQ ID NO: 80; and a heavy chain variable region comprising the amino acid sequence of SEQ ID NO: 89; or
(vii) a light chain variable region comprising the amino acid sequence of SEQ ID NO: 85; and a heavy chain variable region comprising the amino acid sequence of SEQ ID NO: 100; or
(viii) a light chain variable region comprising the amino acid sequence of SEQ ID NO: 85; and a heavy chain variable region comprising the amino acid sequence of SEQ ID NO: 101; or
(ix) a light chain variable region comprising the amino acid sequence of SEQ ID NO: 86; and a heavy chain variable region comprising the amino acid sequence of SEQ ID NO: 100; or
(x) a light chain variable region comprising the amino acid sequence of SEQ ID NO: 86; and a heavy chain variable region comprising the amino acid sequence of SEQ ID NO: 101.

4. The method of claim 1, wherein the anti-IL-36R antibody comprises:
i. a light chain comprising the amino acid sequence of SEQ ID NO: 115; and a heavy chain comprising the amino acid sequence of SEQ ID NO: 125; or
ii. a light chain comprising the amino acid sequence of SEQ ID NO: 115; and a heavy chain comprising the amino acid sequence of SEQ ID NO: 126; or
iii. a light chain comprising the amino acid sequence of SEQ ID NO: 115; and a heavy chain comprising the amino acid sequence of SEQ ID NO: 127; or
iv. a light chain comprising the amino acid sequence of SEQ ID NO: 118; and a heavy chain comprising the amino acid sequence of SEQ ID NO: 125; or
v. a light chain comprising the amino acid sequence of SEQ ID NO: 118; and a heavy chain comprising the amino acid sequence of SEQ ID NO: 126; or
vi. a light chain comprising the amino acid sequence of SEQ ID NO: 118; and a heavy chain comprising the amino acid sequence of SEQ ID NO: 127; or
vii. a light chain comprising the amino acid sequence of SEQ ID NO: 123; and a heavy chain comprising the amino acid sequence of SEQ ID NO: 138; or
viii. a light chain comprising the amino acid sequence of SEQ ID NO: 123; and a heavy chain comprising the amino acid sequence of SEQ ID NO: 139; or
ix. a light chain comprising the amino acid sequence of SEQ ID NO: 124; and a heavy chain comprising the amino acid sequence of SEQ ID NO: 138.

5. The method of claim 1, wherein the anti-IL-36R antibody is spesolimab.

6. The method of claim 1, wherein the therapeutically effective amount of the anti-IL-36R antibody is in the range of about 0.001 to about 1000 mg.

7. The method of claim 1, wherein a second therapeutic agent is administered to the subject before, after, or concurrent with the anti-IL-36R antibody.

8. The method of claim 7, wherein the second therapeutic agent is selected from the group consisting of an anti-bacterial agent, an anti-viral agent, an anti-fungal agent, an anti-IL-36R antibody, an IgE inhibitor, a corticosteroid, a non-steroid anti-inflammatory drug (NSAID), an IL-4R antagonist, and IFN-γ.

* * * * *

UNITED STATES PATENT AND TRADEMARK OFFICE
CERTIFICATE OF CORRECTION

| | |
|---|---|
| PATENT NO. | : 12,098,207 B2 |
| APPLICATION NO. | : 17/376233 |
| DATED | : September 24, 2024 |
| INVENTOR(S) | : Fine et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 262 days.

Signed and Sealed this
Twenty-sixth Day of August, 2025

Coke Morgan Stewart
*Acting Director of the United States Patent and Trademark Office*